US010725049B2

(12) United States Patent
Ackerley et al.

(10) Patent No.: US 10,725,049 B2
(45) Date of Patent: Jul. 28, 2020

(54) METHODS OF DETECTING AND MEASURING GLUTAMINE AND ANALOGUES THEREOF, AND METHODS RELATED THERETO

(71) Applicant: Victoria Link Limited, Kelburn, Wellington (NZ)

(72) Inventors: David Francis Ackerley, Wellington (NZ); Alistair Sinclair Brown, Wellington (NZ); Katherine Jane Robins, Upper Hutt (NZ)

(73) Assignee: VICTORIA LINK LIMITED, Wellington (NZ)

( * ) Notice: Subject to any disclaimer, the term of this patent is extended or adjusted under 35 U.S.C. 154(b) by 0 days.

(21) Appl. No.: 15/894,540

(22) Filed: Feb. 12, 2018

(65) Prior Publication Data

US 2018/0246116 A1 Aug. 30, 2018

Related U.S. Application Data

(63) Continuation of application No. 15/101,883, filed as application No. PCT/NZ2014/050017 on Dec. 5, 2014, now Pat. No. 9,995,750.

(30) Foreign Application Priority Data

Dec. 5, 2013 (NZ) ........................................ 618665
Mar. 28, 2014 (NZ) ........................................ 623117

(51) Int. Cl.
*C12Q 1/527* (2006.01)
*G01N 33/68* (2006.01)
(Continued)

(52) U.S. Cl.
CPC ........ *G01N 33/6812* (2013.01); *C12P 17/165* (2013.01); *C12Q 1/48* (2013.01); *G01N 2333/91171* (2013.01)

(58) Field of Classification Search
CPC ....................................................... C12Q 1/527
See application file for complete search history.

(56) References Cited

U.S. PATENT DOCUMENTS 9,995,750 B2    6/2018  Ackerley
2016/0299151 A1  10/2016  Ackerley

FOREIGN PATENT DOCUMENTS

WO    2012036568    3/2012
WO    2015084189    6/2015

OTHER PUBLICATIONS

Cude et al., "Production of the antimicrobial secondary metabolite indigoidine contributes to competitive surface colonization by the marine *Roseobacter phaeobacter* sp. strain Y41," Applied and Environmental Microbiology, 78(14):4771-4780, May 11, 2012.*

(Continued)

*Primary Examiner* — Rosanne Kosson
(74) *Attorney, Agent, or Firm* — Polsinelli PC

(57) ABSTRACT

Method for the detection of glutamine and its analogues are provided by the present disclosure. Also provided are methods for measuring the levels of glutamine and its analogues, including diagnostic methods. Further provided are methods that utilise glutamine analogues for the synthesis of coloured pigments and other useful agents. The methods comprise the use of a nonribosomal peptide synthetase (NRPS) under conditions to produce an indigoidine or indigoidine-related pigment.

19 Claims, 14 Drawing Sheets

Specification includes a Sequence Listing.

(51) Int. Cl.
*C12Q 1/48* (2006.01)
*C12P 17/16* (2006.01)

(56) References Cited

OTHER PUBLICATIONS

International Application No. PCT/NZ2014/050017; International Preliminary Report on Patentability, dated Jun. 7, 2016; 05 pages.
International Application No. PCT/NZ2014/050017; International Search Report and Written Opinion of the International Searching Authority, dated Feb. 16, 2015; 10 pages.
Li, J. et al., "Medium Optimization by Combining of Response Surfave Methodology and Desirability Function: An Application in in Glutamine Production", Appl Microbiol Biotechnol., 74:563-71, (2007).
Owen, J. et al., "Rapid and Flexible Biochemical Assays for Evaluating 4-Phosphopantetheinyl Transferase Activity", Biochem J., 436:709-17, (2011).
Serrano, M. et al., "Assessment of Plasma Ammonia and Glutamine Concentrations in Urea Cycle Disorders", Clinical Biochemistry, 44:742-4, (2011).
Takashi et al., "Cloning and characterization of a Streptomyces single module type non-ribosomal peptide synthetase catalyzing a blue pigment synthesis," J Biol Chem 282(12):9073-9081, 2007.
U.S. Appl. No. 15/101,883; Applicant Summary of Interview with Examiner, dated Nov. 29, 2017; 1 page.
U.S. Appl. No. 15/101,883; Examiner Initiated Interview Summary dated Jan. 16, 2018; 1 page.
U.S. Appl. No. 15/101,883; Examiner Initiated Interview Summary dated Nov. 14, 2017; 2 pages.
U.S. Appl. No. 15/101,883; Non-Final Office Action dated Nov. 14, 2017; 8 pages.
U.S. Appl. No. 15/101,883; Notice of Allowance dated Apr. 2, 2018; 4 pages.
U.S. Appl. No. 15/101,883; Notice of Allowance dated Feb. 13, 2018; 4 pages.
U.S. Appl. No. 15/101,883; Notice of Allowance dated Jan. 16, 2018; 7 pages.
Brown, A., et al., "A Sensitive Single-Enzyme Assay System Using the Non-Ribosomal Peptide Synthetase BpsA for Measurement of L-glutamine in Biological Samples," Scientific Reports, vol. 7, pp. 1-13 (Jan. 31, 2017).

* cited by examiner

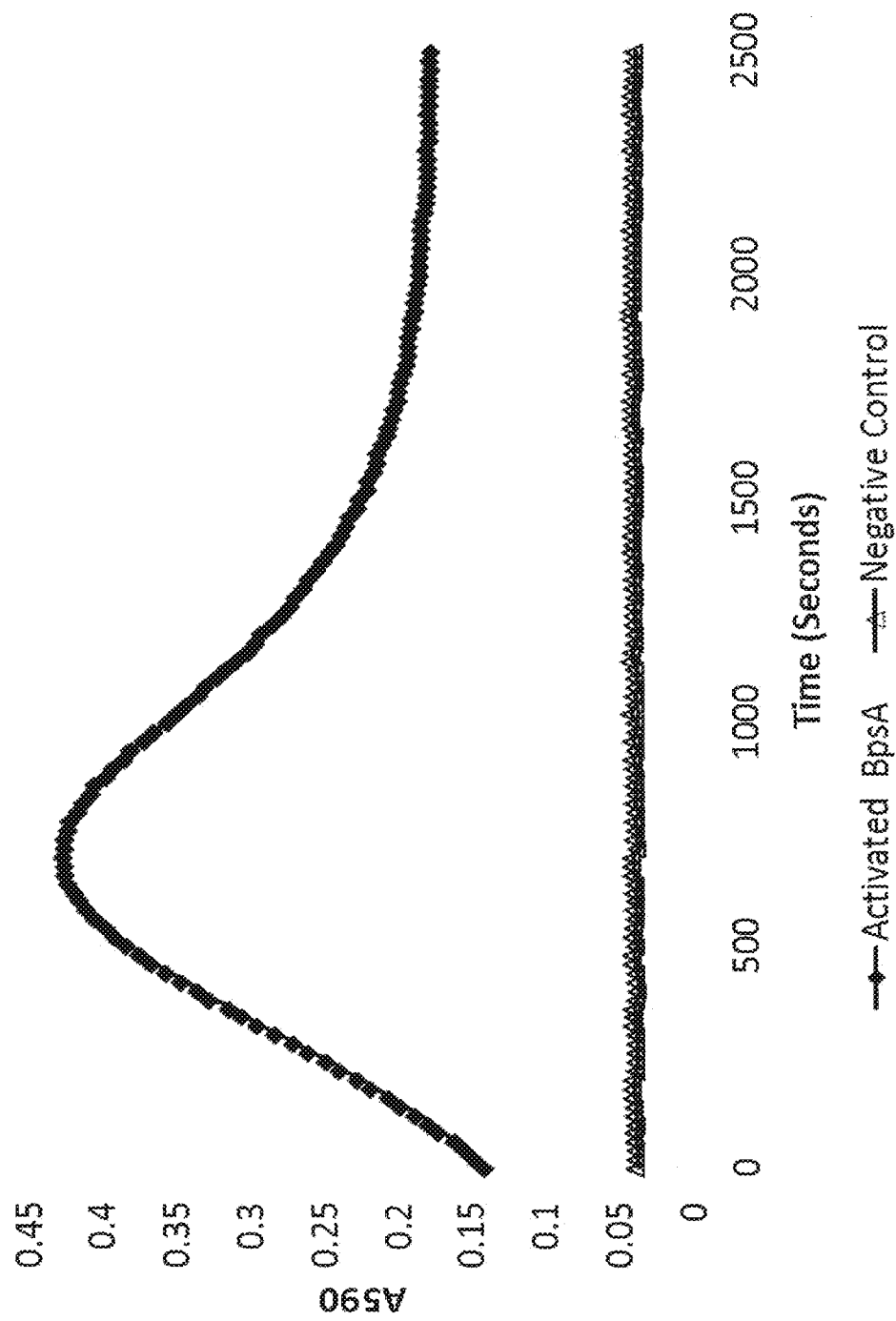

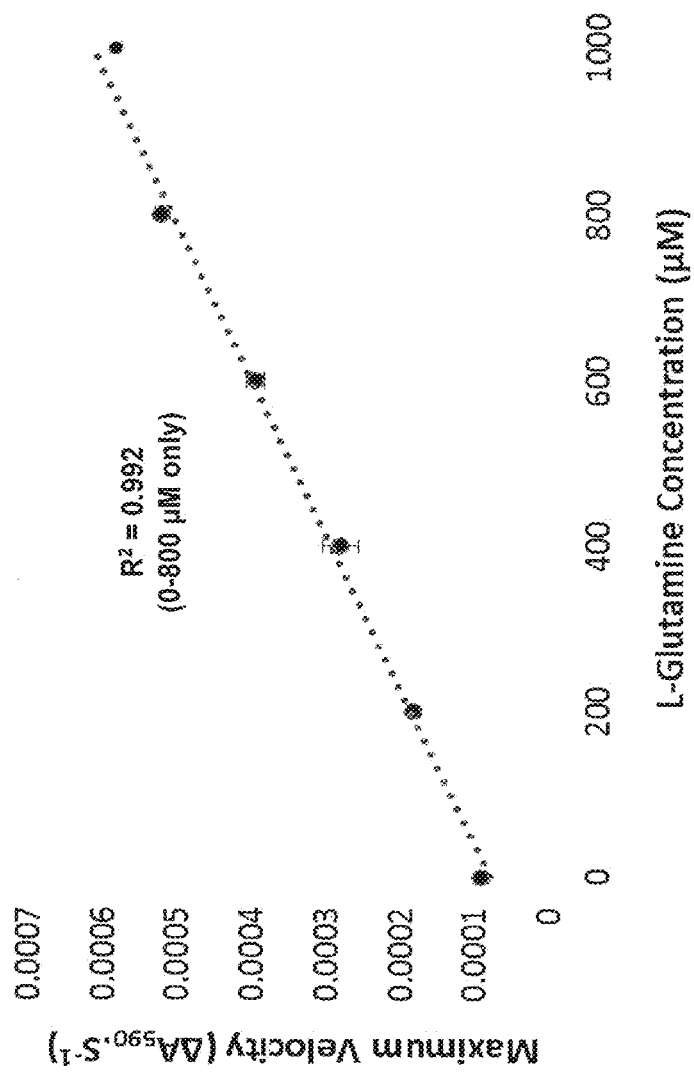

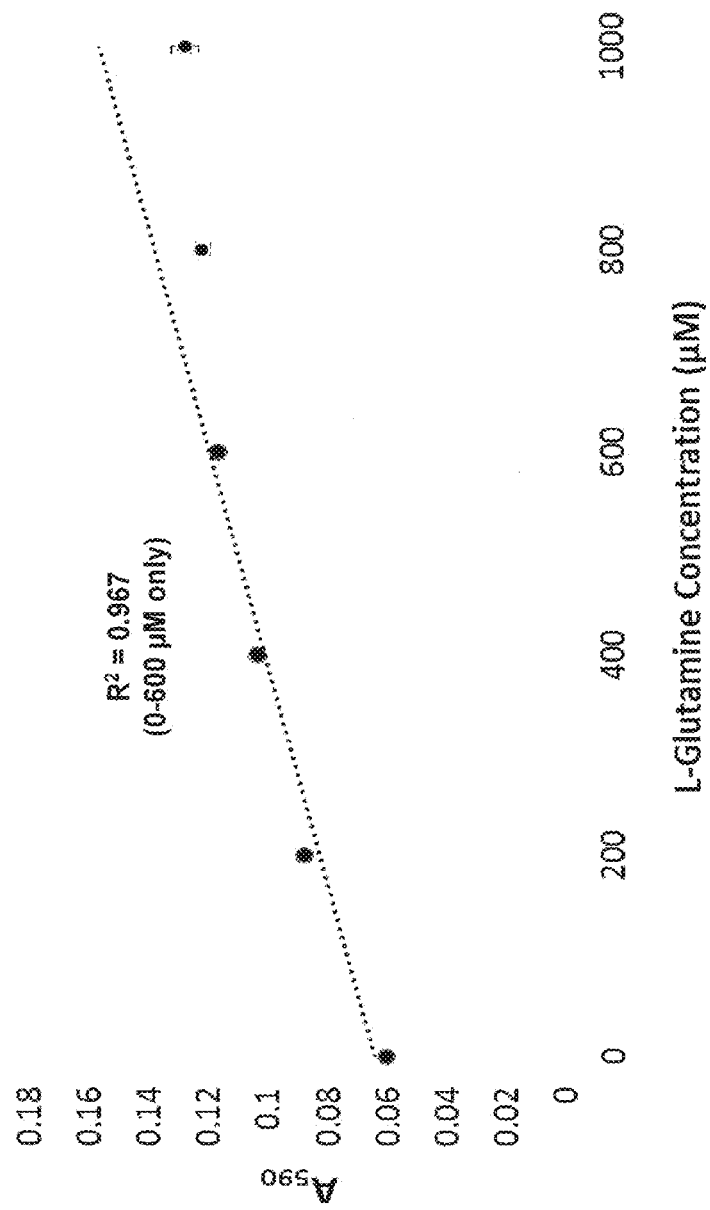

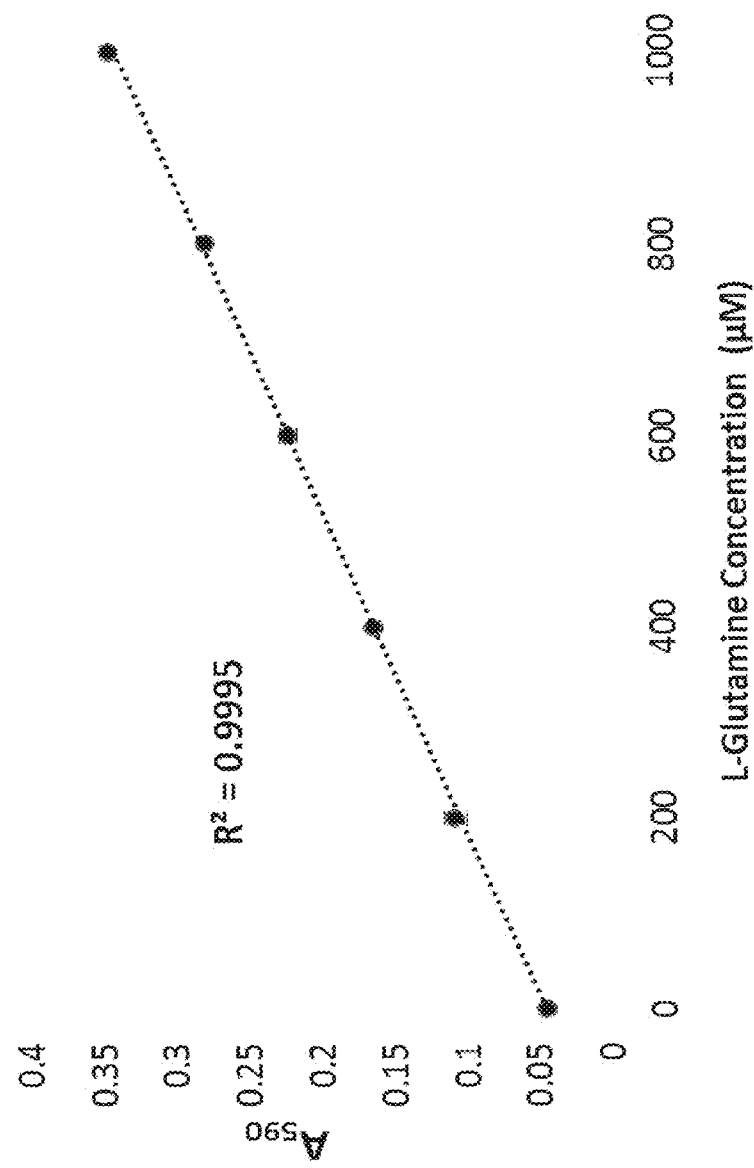

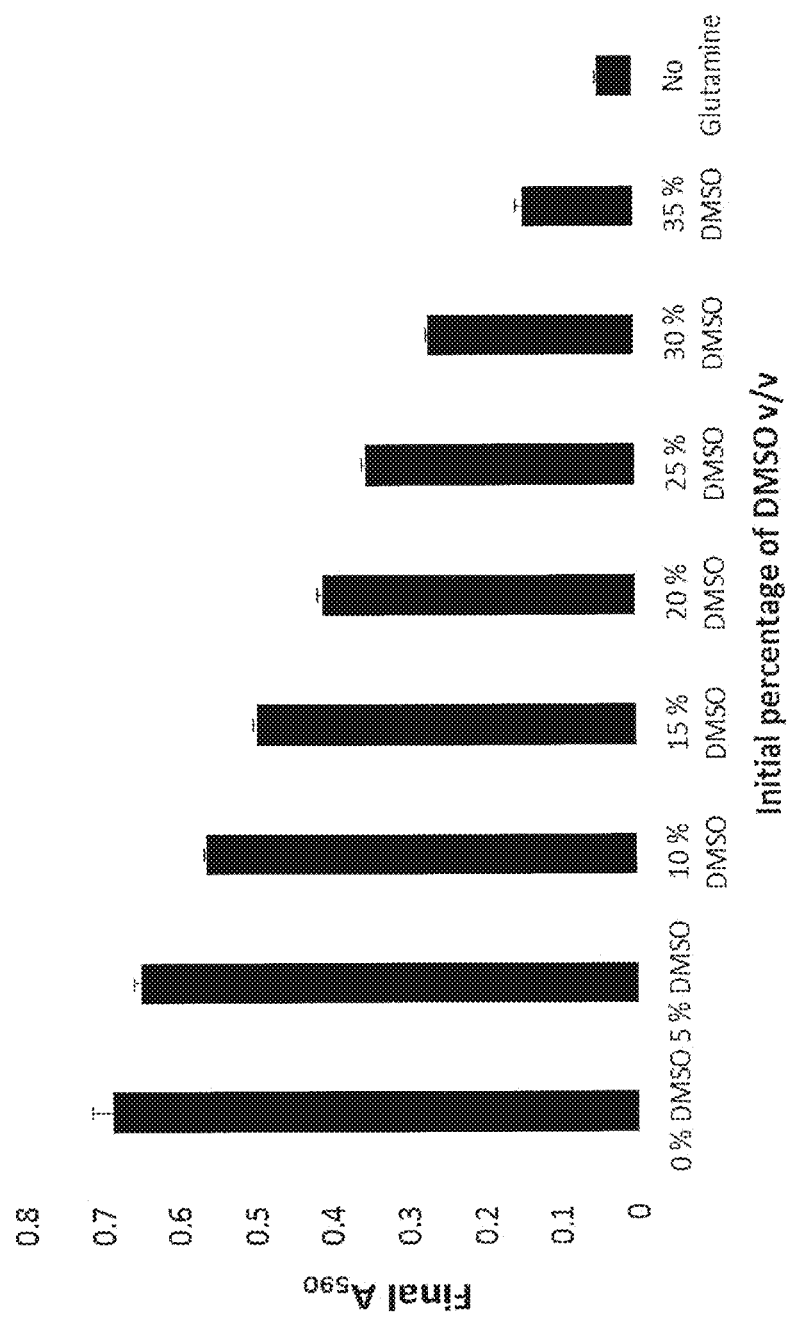

Figure 9A

```
ATGACTCTTCAGGAGACCAGCGTGCTCGAGCCCACCCTGCAGGGGACCACCACGTTGCCCGGCCTGCTCGCCCAG
CGGGTGGCCGAACACCCCGAGGCGATCGCGGTCGCCTACCGGGACGACAAGCTCACCTTCCGCGAGCTCGCGTCC
AGAAGCGCGGCCCTCGCCGACTACCTGGAGCACCTCGGTGTCTCCGCCGACGACTGCGTCGGCCTGTTCGTCGAG
CCGTCGATCGACCTGATGGTCGGCGCCTGGGGCATCCTCAACGCCGGCGCCGCGTACCTGCCGCTGTCCCCGGAG
TACCCCGAGGACCGGCTGCGCTACATGATCGAGAACAGCGAGACGAAGATCATCCTGGCGCAGCAGCGCCTGGTG
TCCCGTCTGCGCGAGCTCGCGCCGAAGGACGTCACCATCGTGACCCTGCGCGAGTCCGAGGCCTTCGTCCGCCCC
GAGGGCACCGAGGCCCCGGCCGCCCGCAGCGCCCGCCCGGACACCCTCGCGTACGTCATCTACACCTCCGGCAGC
ACGGGCAAGCCGAAGGGTGTGATGATCGAGCACCGCAGCATCGTCAACCAGCTCGGCTGGCTGCGCGAGACCTAC
GCGATCGACCGCAGCAAGGTCATCCTCCAGAAGACCCCGATGAGCTTCGACGCCGCCAGTGGGAGATCCTCTCC
CCGGCCAACGGCGCCACCGTCGTCATGGGCGCCCCGGGCGTCTACGCCGACCCCGAGGGCCTCATCGAGACCATC
GTCAAGCACAACGTGACCACCCTCCAGTGCGTCCCGACGCTGCTCCAGGGTCTGATCGACACCGAGAAGTTCCCC
GAGTGCGTCTCCCTCCAGCAGATCTTCAGCGGTGGCGAGGCCCTCTCCCGCCTGCTGGCGATCCAGACCACGCAG
GAGATGCCCGGCCGGCGCTCATCAACGTCTACGGGCCGACCGAGACGACGATCAACTCGTCCTCGTTCCCCGTC
GACCCCGCCGACCTGGACGAGGGACCGCAGTCCATCTCCATCGGCTCCCGGTGCACGGCACCACGTACCACATC
CTTGACAAGGAGACCCTCAAGCCGGTCGGCGTCGGTGAGATCGGCGAGCTGTACATCGGCGGCATCCAGCTGGCC
CGCGGCTACCTGCACCGCGACGACCTGACCGCCGAGCGCTTCCTGGAGATCGAGCTCGAGGAGGGCGCCGAGCCC
GTCCGCCTGTACAAGACGGGCGACCTCGGCCAGTGGAACAACGACGGCACCGTGCAGTTCGCCGGCCGCGCCGAC
AACCAGGTCAAGCTGCGCGGCTACCGCGTCGAGCTCGACGAGATATCCCTGGCGATCGAGAACCACGACTGGGTC
CGCAACGCCGCCGTCATCGTCAAGAACGACGGCCGCACCGGCTTCCAGAACCTGATCGCCTGCATCGAGCTGAGC
GAGAAGGAAGCCGCCCTGATGGACCAGGGCAACCACGGCTCCCACCACGCGTCGAAGAAGAGCAAGCTCCAGGTC
AAGGCGCAGCTGTCCAACCCGGGCCTGCGCGACGACGCCGAGCTGGCCGCCCGCCCGGCCTTCGACCTGGAGGGC
GCCGAGCCCACCCCCGAGCAGCGCGCCCGGGTCTTCGCCCGCAAGACGTACCGCTTCTACGAGGGCGGCGCCGTC
ACCCAGGCCGACCTGCTGGGCCTGCTGGGCGCCACGGTCACCGCCGGCTACTCGCGCAAGGCGGCCGACCTGGCC
CCCGCCGAACTCGGCCAGATCCTGCGCTGGTTCGGCCAGTACATCAGCGAGGAGCGGCTCCTGCCGAAGTACGGC
TACGCCTCCCCGGGCGCGCTGTACGCGACGCAGATGTACTTCGAGCTGGAGGGCGTCGGCGGTCTGAAGCCGGGC
TACTACTACTACCAGCCGGTCCGCCACCAGCTCGTCCTCATCAGCGAGCGCGAGGCCACCGGCAAGGCCACGGCG
CAGATCCACTTCATCGGCAAGAAGAGCGGCATCGAGCCGGTCTACAAGAACAACATCCTCGAGGTCCTGGAGATC
GAGACCGGCCACATGGTCGGCCTCTTCGAGCAGATCCTGCCGGCCTACGGCCTCGACATCCACGACCGCGCCTAC
GAGCCGGCCGTCAAGGACCTGCTCGACGTCGCCGACGAGGACTACTACCTGGGCACCTTCGAGCTGGTCCCGCAC
GCGGGCGCGCGCGACGACCAGGCCGAGGTCTACGTCCAGACGCACGGCGGAAAGGTCGCCGGCCTGCCCGAGGGC
CAGTACCGCTACGAGAACGGCGAGCTGACCCGCTTCTCGGACGACATCGTCCTCAAGAAGCACGTCATCGCGATC
AACCAGTCGGTGTACCAGGCCGCCAGCTTCGGCATCAGCGTCTACAGCCGCGCCGAGGAGGAGTGGCTGAAGTAC
ATCACCCTCGGCAAGAAGCTCCAGCACCTCGATGATGAACGGGCTGAACCTGGGCTTCATGTCCTCGGGCTACAC
TCCAAGACGGGCAACCCGCTGCCGGCCTCGCGCCGCATGGCGCCGTCCTCGCCAACGGCGTCGACGCGCC
CCGATGTACTTCTTCGTCGGCGGCCGCATCAGCGACGAGCAGATCGGCCACGAGGGCATGCGCGAGGACAGCGTC
CACATGCGCGGTCCGGCCGAGCTCATCCGCGACGACCTCGTCAGCTTCCTCCCGGACTACATGATCCCCAACCGG
GTCGTGGTCTTCGACCGGCTGCCGCTGTCCGCCAACGGCAAGATCGACGTCAAGGCGCTCGCCGCCTCCGACCAG
GTCAACGCCGAGCTCGTCGAGCGCCCCTTCGTCGCCCCGCGCACGGAGACGGAGAAGGAGATCGCGGCGG
TCTGGGAGAAGGCCCTGCGCCGCGAGAACGCCTCCGTCCAGGACGACTTCTTCGAGTCGGGCGGCAAC
TCGCTGATCGCCGTCGGCCTCGTCCGCGAGCTCAACGCGCGCCTGGGCGTCTCCCTGCCGCTGCAGAG
CGTCCTGGAGTCCCCGACCATCGAGAAGCTGGCCCGCCGCCTGGAGCGCGAGGTCGCCCAGGAGTCCTCG
CGCTTCGTCCGCCTGCACGCGGAGACCGGCAAGGCCCGGCCCGTGATCTGCTGGCCGGGTCTGGCGGCTACCCG
ATGAACCTGCGCAGCCTGGCCGGCGAGATCGGCTCGGCCGCTCGTTCTACGGCGTCCAGTCCTACGGCATCAAC
GAGGGCGAGACCCCGTACGAGACCATCACCGAGATGGCCAAGAAGGACATCGAGGCCCTCAAGGAGATCCAGCCG
GCCGGCCCCTACACCCTGTGGGCTACTCCTTCGGCGCCCGCGTGGCCTTCGAGACCGCCTACCAGCTGGAGCAG
GCGGGCGAGAAGGTGGACAACCTCTTCCTGATCGCCCCGGGCTCCCCGAAGGTGCGCGCCGAGAACGGCAAGGTG
TGGGGCCGCGAGGCGTCCTTCGCCAACCCCGCTACACCACCATCCTGTTCTCGGTCTTCACCGGCACCATTTCC
GGTCCGGACCTGGACCGGTGCCTGGAGACCGTGACGGACGAGGCCCTTCGCCGAGTTCATCAGCGAGCTCAAG
GGAATCGACGTCGACCTCGCCCGCCGGATCATCTCGGTCGTGGGCCAGACGTACGAATTCGAGTACTCCTTCCAC
GAGCTGGCCGAGCGCACCCTCCAGGCGCCGATCAGCATCTTCAAGGCCGTGGGCGACGACTACTCGTTCCTGGAG
AACAGCAGCGGCTACTCGGCCGAGCCGCCGACGGTCATCGACCTCGACGCCGACCACTACAGCCTGCTGCGCGAG
GACATCGGCGAGCTGGTGAAGCACATCCGCTACCTGCTCGGCGAGTGA
```

Figure 9B

MTLQETSVLEPTLQGTTTLPGLLAQRVAEHPEAIAVAYRDDKLTFRELASRSAALADYLEHLGVSADDCVGLFVE
PSIDLMVGAWGILNAGAAYLFLSPEYPEDRLRYMIENSETKIILAQQRLVSRLRELAPKDVTIVTLRESEAFVRP
EGTEAPAARSARPDTLAYVIYTSGSTGKPKGVMIEHRSIVNQLGWLRETYAIDRSKVILQKTPMSFDAAQWEILS
PANGATVVMGAPGVYADPEGLIETIVKHNVTTLQCVPTLLQGLIDTEKFPECVSLQQIFSGGEALSRLLAIQTTQ
EMPGRALINVYGPTETTINSSSFPVDPADLDEGPQSISIGSPVHGTTYHILDKETLKPVGVGEIGELYIGGIQLA
RGYLHRDDLTAERFLEIELEEGAEPVRLYKTGDLGQWNNDGTVQFAGRADNQVKLRGYRVELDEISLAIENHDWV
RNAAVIVKNDGRTGFQNLIACIELSEKEAALMDQGNHGSHHASKKSKLQVKAQLSNPGLRDDAELAARPAFDLEG
AEPTPEQRARVFARKTYRFYEGGAVTQADLLGLLGATVTAGYSRKAADLAPAELGQILRWFGQYISEERLLPKYG
YASPGALYATQMYFELEGVGGLKPGYYYYQPVRHQLVLISEREATGKATAQIHFIGKKSGIEPVYKNNILEVLEI
ETGHMVGLFEQILPAYGLDIHDRAYEPAVKDLLDVADEDYYLGTFELVPHAGARDDQAEVYVQTHGGKVAGLPEG
QYRYENGELTRFSDDIVLKKHVIAINQSVYQAASFGISVYSRAEEEWLKYITLGKKLQHLMMNGLNLGFMSSGYS
SKTGNPLPASRRMDAVLGANGVDSAPMYFFVGGRISDEQIGHEGMREDSVHMRGPAELIRDDLVSFLPDYMIPNR
VVVFDRLPLSANGKIDVKALAASDQVNAELVERPFVAPRTETEKEIAAVWEKALRRENASVQDDFFESGGN
SLIAVGLVRELNARLGVSLPLQSVLESPTIEKLARRLEREVAQESSRFVRLHAETGKARPVICWPGLGGYP
MNLRSLAGEIGLGRSFYGVQSYGINEGETPYETITEMAKKDIEALKEIQPAGFYTLWGYSFGARVAFETAYQLEQ
AGEKVDNLFLIAPGSPKVRAENGKVWGREASFANRGYTTILFSVFTGTISGPDLDRCLETVTDEASFAEFISELK
GIDVDLARRIISVVGQTYEFEYSFHELAERTLQAPISIFKAVGDDYSFLENSSGYSAEPPTVIDLDADHYSLLRE
DIGELVKHIRYLLGE

METHODS OF DETECTING AND MEASURING GLUTAMINE AND ANALOGUES THEREOF, AND METHODS RELATED THERETO

RELATED APPLICATIONS

This application is a continuation of U.S. patent application Ser. No. 15/101,883, filed on 3 Jun. 2016, which is a 371 application of International Application Number PCT/NZ2014/050017, filed on 5 Dec. 2014, which claims the benefit of New Zealand Patent Application No. 618665 filed on 5 Dec. 2013, and New Zealand Patent Application Number 623117 filed on 28 Mar. 2014, which are hereby incorporated by reference herein in their entirety.

FIELD OF THE INVENTION

The present disclosure relates to methods of detecting glutamine and its analogues, as well as methods of measuring levels of glutamine and its analogues. Also related are methods of using glutamine analogues for the synthesis of coloured pigments and other useful agents.

BACKGROUND OF THE INVENTION

Glutamine (Gln) is one of the twenty ammo acids encoded by the standard genetic code. The glutamine side chain is an amide; it is formed by replacing a side-chain hydroxyl of glutamic acid with an amine functional group.

Glutamine is the most abundant free amino add in the blood stream with concentrations in the range of 500 to 750 µM (Walsh et al., 1998). Yet, the majority of dietary glutamine does not enter the blood stream under normal conditions. This is because most of it is utilised as respiratory fuel by the epithelial cells in the small intestines. Both the lungs and the brain produce small amounts of glutamine (Newsholme, 2001). Skeletal muscles produce the majority of glutamine in the body, as they contain over 90% of the total glutamine (Newsholme, 2001).

Glutamine has a diverse range of functions in the human body. It is involved in nitrogen transport in the brain (Young & Ajami, 2001). Glutamine has a key role in the immune system. Lymphocyte proliferation is dependent on extracellular glutamine levels. Studies have also shown that macrophage activity is suppressed when glutamine levels are lowered. Glutamine is a key fuel source for immune cells (Newsholme, 2001).

Glutamine is found in foods high in proteins, such as fish, red meat. beans, and dairy products. Glutamine supplements are used in weightlifting, bodybuilding, endurance and other sports, as well as by those who suffer from muscular cramps or pain, particularly elderly people. Glutamine is used mainly in the diet to replenish the body's stores of amino acids that have been used during workouts or everyday activities. Studies examining the effects of excessive consumption of glutamine have thus far proved inconclusive. Supplementation is normally considered beneficial because amino acid replenishment is required after prolonged periods of exercise. For example, where a workout or exercise requires use of amino acids, this creates a need for amino acid stores to be replenished. See, e.g., Castell & Newsholme, 1997. For this reason, glutamine is recommended during fasting, or for people who suffer from physical trauma, immune deficiencies, or cancer.

There is a significant body of evidence that links glutamine-enriched diets with improvement of intestinal conditions, for example, aiding maintenance of gut barrier function, addressing intestinal cell proliferation and differentiation, as well as generally reducing septic morbidity and the symptoms of irritable bowel syndrome. See, e.g., Wischmeyer, 2006. The cleansing properties of glutamine are thought to stem from the fact that the intestinal extraction rate of glutamine is higher than that for other amino acids. This was discovered by comparing plasma concentration within the gut between glutamine-enriched and non-glutamine-enriched diets. Glutamine is therefore thought to be a key component for alleviating problems in the gastrointestinal tract. Yet, the concentration of glutamine varies in different varieties of food, and it can be difficult to quantify the clinical benefit that is derived.

In addition, glutamine supplements can reduce healing time after operations. See, e.g., Morlion et al., 1998. Hospital wailing times after abdominal surgery have been reduced by providing parenteral nutrition regimens containing amounts of glutamine to patients. Clinical trials have revealed that patients on glutamine supplementation regimes show improved nitrogen balances, generation of cysteinyl-leukotrienes from polymorphonuclear neutrophil granulocytes, and improved postoperative lymphocyte recovery and intestinal permeability, in comparison to patients lacking glutamine supplementation. These noted benefits were observed without any concomitant side effects.

Plasma glutamine levels fall during times of stress such as sepsis, injury. burns, and premature birth. This is because in the inflammatory state the glutamine consumption by immune cells and other tissues increase. This outstrips the supply of glutamine and results in reduced levels of glutamine in the blood, immunological tissue, and muscles. If the plasma concentration fails below 400 µM, it is termed glutamine-deficient (Newsholme, 2001). Exercise also has an effect on plasma glutamine levels. Both high intensity training and endurance training have been shown to reduce the levels of Glutamine in the blood (levels are usually lower than 500 µM) (Walsh et al, 1998). Glutamine levels in the blood plasma are consistently higher in patients with urea cycle disorders (Serrano et al., 2011).

It has been suggested that high levels of glutamine and alanine along with lower levels of arginine and citrulline in the blood plasma can be used to detect the urea cycle disorders N-acetylglutamate synthetase deficiency (NAGSD) and carbamylphosphate synthetase deficiency (CPSD) (Serrano et al., 2011). It has also been suggested that high levels of glutamine in blood plasma is a possible biomarker of OTCD, a urea cycle disorder that affects 1 in 14000 births (Trinh et al., 2003). Lower levels of glutamine in the blood also have the potential to be an indicator for overtraining syndrome (OTS). Studies have shown that glutamine levels are lower than the normal base line in athletes suffering from overtraining (Walsh et al., 1998). Thus, reduced glutamine in the blood serum may be considered as a biomarker of overtraining (Agostini et al., 2010; Petibois et al., 2002; McKenzie, 1999).

Very low levels of L-glutamine in the brain may be symptomatic of Alzheimer's disease (see, e.g., Chen & Herrup, 2012) or other neurodegenerative disorders (Tsuroka et al., 2013), while very low levels in serum or saliva are associated with rapidly growing tumours (Iketa et al., 2012; Tan et al., 2013). Very high levels of L-glutamine in urine may be symptomatic of aminoaciduria from muscle or tissue breakdown due to range of conditions, such as burns, surgery, wasting diseases, or infection. Moreover, altered levels of glutamine analogues in urine may be associated with various medical treatments or conditions, including metabolic and renal diseases.

For medical diagnostics and scientific research, glutamine levels are commonly assessed by mass spectrometry (see, e.g., Trinh et al., 2003: Darmaun, et al., 1985). There are glutamine measuring kits available from a range of suppliers (see, e.g., Sigma-Aldrich, Stock No. GLN-2: sec also, Bioassay Systems, Catalogue No. EGLN-100). There are also published methods using an *Escherichia coli* based biosensor for detecting glutamine levels in plants (Tessaro et al., 2012). There are other published methods of measuring glutamine in a liquid sample using a membrane with immobilised glutaminase and glutamate oxidase (WO 88/10424).

Glutamine is also produced commercially for use in pharmaceuticals and nutritional supplements. Current estimated production of L-glutamine is over 2000 tons annually (Kusumoto, 2001). Several bacterial strains have been reported for glutamine production, including *Brevibacterium* flavin (Tsuchida et al., 1987) and *Flavobacterium rigense* (Nabe et al., 1981). However, the most commonly used strain for large scale amino acid production is aerobic actinomycete *Corynebacterium glutamicum* (Hermann, 2003).

*C. glutamicum* was discovered as a glutamate producer in the 1950s, with industrial production of L-glutamine starting in the late 1960s. The wild-type strain of *C. glutamicum* has high levels of endogenous L-glutamate as well as L-glutamine (L-gln) (Rehm and Burkovski, 2011). Both L-glutamate and L-glutamine can be excreted by certain optimized producer strains (Rehm and Burkovski, 2011; Kusumoto et at, 2001). In industrial production, *C. glutamicum* produces bulk quantities of L-glutamate and L-lysine, as well as smaller amounts of other amino acids, including L-glutamine (Hermann 2003).

During bacterial production, glutamate can be converted to L-glutamine under the right fermentation conditions. This includes the presence of the glnA gene, coding for glutamine synthetase I (GSI), which catalyses the reaction (Jakoby et al., 1997). The glnA gene is native to *C. glutamicum*, but is overexpressed in strains used for glutamine production. There is also an improved variant of this gene, termed glnA', which was produced by site directed mutagenesis and includes the encoded mutation Y405F (Jakoby et al., 1999). The wild-type glnA gene is most active during nitrogen starvation and down regulated by high nitrogen levels, as it is involved in the nitrogen regulation pathway. In contrast, the variant is not down regulated in the presence of nitrogen.

For commercial production, different methods have been used to maximise and measure glutamine levels. According to one method, the amount of both L-glutamate and L-glutamine is increased by introducing a gene encoding haemoglobin that binds oxygen under hypoxic conditions, as the conversion to L-glutamine is a very high oxygen/energy reaction. The presence of the haemoglobin gene increases the production of both amino acids by 25-30% (Liu et al., 2008). According to this method, L-glutamate and L-glutamine are assayed by HPLC performed on the supernatant of the cells. The ratio of L-glutamine to L-glutamate is obtained, which is important for commercial production. With such production, L-glutamate is considered a by-product and can make downstream processing more difficult and expensive (Li et al., 2007).

According to another method, the activity of glutamine synthetase enzyme itself is assessed rather than the actual amount of L-glutamine being produced. This method includes in vitro assays to measure the activity of the glutamine synthetase enzyme by looking at NADH depletion (Wakisaka et al., 1990). Yet another method attempts to optimise L-glutamine production through optimization of levels of glucose versus $(NH_4)_2SO_4$ levels. This method utilises an enzyme based assay and Biochemistry Analyzer YSI 2700 (Yellow Springs Instrument Co., USA; Li et al., 2007). Older methods for measuring glutamine have used quantitative paper chromatography (Tsuchida et al., 1987), or have assessed glutamine synthetase activity using glutamate together with an alternative substrate (e.g. hydroxylamine) in place of ammonia. In the case of hydroxylamine this yields an alternative coloured product, γ-glutamylhydroxamate (Nabe et al., 1981).

Glutamine analogues are also widely used in industry, scientific research, and medicine. Alanyl-glutamine is a more stable analogue of glutamine that is generally used in tissue culture. It is more heat stable and less ammoniagenic than glutamine (see Sigma Aldrich, Product Information Sheet for A8185). Other analogues of glutamine have been noted as potential anti-cancer compounds, including 6-diazo-5-oxo-L-norleucine (L-DON), azaserine, and acivicin (Ahluwalia, 1990; Szkudlinski et al., 1990).

Given the importance of glutamine and glutamine analogues in industrial production, nutrition, medicine, and basic scientific research, there is significant interest in developing new methods for identifying and measuring these compounds.

SUMMARY OF THE INVENTION

As described herein, the present inventors have developed assays using an enzyme known as BpsA (blue pigment synthase A) to detect and measure the concentration of glutamine and glutamine analogues.

The methods of the invention are based on the 2:1 ratio of conversion of L-glutamine into the blue pigment indigoidine by BpsA enzyme. The inventors have also shown that activated BpsA is able to condense analogues of glutamine into indigoidine-like pigments. This activity can be used to assay levels of glutamine analogues in an equivalent fashion to the measurement of glutamine itself. Moreover, these methods provide a simple biosynthetic route to novel chemical structures based on a core indigoidine scaffold.

In one aspect, the invention encompasses a method of measuring the concentration of L-glutamine in a sample, comprising: incubating the sample with an activated pigment-producing NRPS under conditions to produce indigoidine pigment; and quantifying the amount of indigoidine pigment produced.

Other aspects of this method are set out as follows. The pigment-producing NRPS may be BpsA or a functional variant thereof. The BpsA or the functional variant thereof may be activated in vivo and isolated prior to incubation. The BpsA or the functional variant thereof may be activated prior to or following isolation of the BpsA or the functional variant thereof. The sample may be a biological sample selected from the group consisting of a blood sample, a urine sample, a saliva sample, a cerebrospinal fluid sample, a lymph fluid sample, a eukaryotic cell culture sample, and a bacterial cell culture sample.

In one other aspect, the invention encompasses a method of measuring the concentration of a glutamine analogue in a sample, comprising: incubating the sample with an activated pigment-producing NRPS under conditions to produce an indigoidine-related pigment; and quantifying the amount of indigoidine-related pigment produced.

Other aspects of this method are set out as follows. The pigment-producing NRPS may be BpsA or a functional variant thereof. The BpsA or the functional variant thereof may be activated prior to or following isolation of the BpsA or the functional variant thereof. The sample may be a biological sample selected from the group consisting of a blood sample, a urine sample, a saliva sample, a cerebrospinal fluid sample, a lymph fluid sample, a eukaryotic cell culture sample, and a bacterial cell culture sample. The Glutamine analogue may be selected from the group consisting of glycyl-Glutamine, N-trifluoroacetyl-L-glutamine, alanyl-glutamine, indoleacetyl glutamine, N-acetylglutamine, phenylacetyl-L-glutamine, and glutamine-terminating peptides or polypeptides.

In yet one other aspect, the invention encompasses a method of diagnosing a condition or disorder associated with altered levels of L-glutamine in a test subject, comprising: providing a biological sample from the test subject; incubating the biological sample with an activated pigment-producing NRPS under conditions to produce indigoidine pigment; measuring the amount of indigoidine pigment produced by incubation with the biological sample; wherein an increase or decrease in the amount of pigment relative to a control or standard amount indicates altered levels of L-glutamine.

Other aspects of this method are set out as follows. The pigment-producing NRPS may be BpsA or a functional variant thereof. The BpsA or the functional variant thereof may be activated prior to or following isolation of the BpsA or the functional variant thereof. The biological sample may be a blood sample, urine sample, a saliva sample, a cerebrospinal fluid sample, or a lymph fluid sample, The condition or disorder may be selected from the group consisting or overtraining syndrome, urea cycle disorders, Alzheimer's disease and other neurodegenerative disorders, cancers, and aminoaciduria and related conditions.

In one other aspect, the invention encompasses a method of diagnosing a condition or disorder associated with altered levels of a glutamine analogue in a test subject, comprising: providing a biological sample from the test subject; incubating the biological sample with an activated pigment-producing NRPS under conditions to produce an indigoidine-related pigment; and measuring the amount of indigoidine-related pigment produced by incubation with the biological sample; wherein an increase or decrease in the amount of pigment relative to a control or standard amount indicates altered levels of the glutamine analogue.

Other aspects of this method arc set out as follows. The pigment-producing NRPS may be BpsA or a functional variant thereof. The BpsA or the functional variant thereof may be activated prior to or following isolation of the BpsA or the functional variant thereof. The biological sample may be a urine sample. The glutamine analogue may be selected from the group consisting of indoleacetyl glutamine, N-acetylglutamine, and phenylacetyl-L-glutamine. The condition or disorder may be selected from the group consisting of Hartnup disease, autosomal dominant polycystic kidney disease, renal tubal injury, aminoacylase deficiency, and uremia.

In still one other aspect the invention encompasses a method of producing an indigoidine-related pigment molecule, comprising: incubating a glutamine analogue with an activated pigment-producing NRPS under conditions to produce the indigoidine-related pigment molecule.

Other aspects of this method are set om as follows. The pigment-producing NRPS may be BpsA or a functional variant thereof. The BpsA or the functional variant thereof may be activated prior to or following isolation of the BpsA or the functional variant thereof. The glutamine analogue may be selected from the group consisting of glycyl-glutamine, N-trifluoroacetyl-L-glutamine, alanyl-glutamine, indoleacetyl glutamine, N-acetylglutamine, phenylacetyl-L-glutamine, and glutamine-terminating peptides or polypeptides.

In even one other aspect, the invention encompasses a method of identifying a bacterial cell having altered L-glutamine production, comprising: providing a bacterial cell that synthesises L-glutamine; incubating the bacterial cell with an activated pigment-producing NRPS under conditions to produce indigoidine pigment; measuring the amount of indigoidine pigment produced by incubation with the bacterial cell; wherein an increase or decrease in the amount of pigment relative to a control or standard amount indicates altered levels of L-glutamine production.

Other aspects of this method are set out as follows. The pigment-producing NRPS may be BpsA or a functional variant thereof. The BpsA or the functional variant thereof may be activated prior to or following isolation of the BpsA or the functional variant thereof. The bacterial cell may be a mutant or variant cell. The bacterial cell may be produced by targeted or random mutagenesis.

In one further aspect, the invention encompasses a method of identifying a bacterial cell having altered glutamine analogue production, comprising: providing a bacterial cell that synthesises a glutamine analogue; incubating the bacterial cell with an activated pigment-producing NRPS under conditions to produce an indigoidine-related pigment; measuring the amount of the indigoidine-related pigment produced by incubation with the bacterial cell; wherein an increase or decrease in the amount of pigment relative to a control or standard amount indicates altered levels of the glutamine analogue.

Other aspects of this method are set out as follows. The pigment-producing NRPS may be BpsA or a functional variant thereof. The BpsA or the functional variant thereof may be activated prior to or following isolation of the BpsA or the functional variant thereof. The glutamine analogue may be a glutamine-terminating peptide or polypeptide. The glutamine analogue may be alanyl-glutamine or another glutamine-terminating dipeptide. The bacterial cell may be a mutant or variant cell. The bacterial cell may be produced by targeted or random mutagenesis.

The foregoing brief summary broadly describes the features and technical advantages of certain embodiments of the present invention. Further technical advantages will be described in the detailed description of the invention and examples that follows.

Novel features that are believed to be characteristic of the invention will be better understood from the detailed description of the invention when considered in connection with any accompanying figures and examples. However, the figures and examples provided herein are intended to help illustrate the invention or assist with developing an understanding of the invention, and are not intended to limit the invention's scope.

BRIEF DESCRIPTION OF THE DRAWINGS

FIG. 2: BpsA activated in mixed cell lysates by the PPTase PcpS, prior to purification, can synthesise indigoidine. Each data point represents the mean of triplicate repeats. The graph displays the first 2500 seconds of the reaction, post-addition of the substrate L-glutamine.

FIG. 3A through FIG. 3C: Generation of standard curves from BpsA kinetic assays. FIG. 3A: The concentration of L-glutamine in the media affects both the velocity of the reaction and the initial maximum $A_{590}$ value that is achieved prior to precipitation of indigoidine. Each data point represents the mean of triplicate repeats. The graph displays the first 1500 seconds of the reaction. The solid line indicates the maximum slope (i.e., maximum velocity; calculated using the slope function of Microsoft® Excel) of indigoidine synthesis for the reaction curve of the 1000 µM L-glutamine standard; and the dashed line indicates the maximum $A_{590}$ value achieved for the 1000 µM L-glutamine standard. FIG. 3B: Standard curve derived from the maximum velocity data for each sample in FIG. 3A. A near-linear standard curve can be generated up to 800 µM, as indicated by the trend line. The error bars represent ±1 standard deviation between the triplicate assay data. FIG. 3C: Standard curve derived from the maximum $A_{590}$ values for each sample in FIG. 3A. A near-linear standard curve can be generated up to 600 µM, as indicated by the trend line. The error bars represent ±1 standard deviation between the triplicate assay data.

FIG. 4: The $A_{590}$ value of each well was measured once, at the conclusion of the reaction (post 45 min incubation) and post addition of a final concentration of 83% DMSO to solubilise all indigoidine present. Each data point represents the mean of triplicate repeats for each standard sample. Error bars represent ±1 standard deviation.

FIG. 5A and FIG. 5B: The ability of purified holo-BpsA to synthesise indigoidine in the presence of varying percentages of DMSO. FIG. 5A: Pre-activated BpsA was incubated with varying percentages of DMSO (v/v, as indicated) in the final reaction volume. Indigoidine production was measured every twenty seconds for one hour. Each data point represents the mean of triplicate repeats. FIG. 5B: The $A_{590}$ value of each well was measured once, at the conclusion of the reaction (post 45 min incubation) and post addition of additional DMSO to a level sufficient to solubilise all indigoidine present (>78% final concentration v/v). Each data point represents the mean of triplicate repeats. Error bars represent ±1 standard deviation.

FIG. 8A: Left: Substrate to product conversion equation for indigoidine synthesised from two molecules of L-glutamine. Right: Photograph of indigoidine after resuspension in DMSO. FIG. 8B: Left: Predicted substrate to product conversion equation for the indigoidine analogue synthesised from two molecules of L-glycine-L-glutamine (glycyl-glutamine). Right: Photograph of the corresponding indigoidine analogue post-resuspension in DMSO. FIG. 8C: Left; Predicted substrate to product conversion equation for the indigoidine analogue synthesised from two molecules of L-alanine-L-glutamine (alanyl-glutamine). Right: Photograph of the corresponding indigoidine analogue post-resuspension in DMSO. FIG. 8D: Left: Predicted substrate to product conversion equation for the indigoidine analogue synthesised from two molecules of N-trifluoracetyl-L-glutamine. Right: Photograph of the corresponding indigoidine analogue post-resuspension in DMSO. FIG. 8E: Graph indicating the final mean $A_{590}$ of triplicate reactions for each glutamine analogue and no substrate control. Error bars indicate ±1 standard deviation. Inset: Repeated images of the corresponding indigoidine analogues post-resuspension in DMSO.

FIG. 9A and FIG. 9B: BpsA sequence information. FIG. 9A: BpsA polynucleotide sequence (SEQ ID NO:1). FIG. 9B: BpsA polypeptide sequence (SEQ ID NO:2).

DETAILED DESCRIPTION OF THE INVENTION

Figure 1:
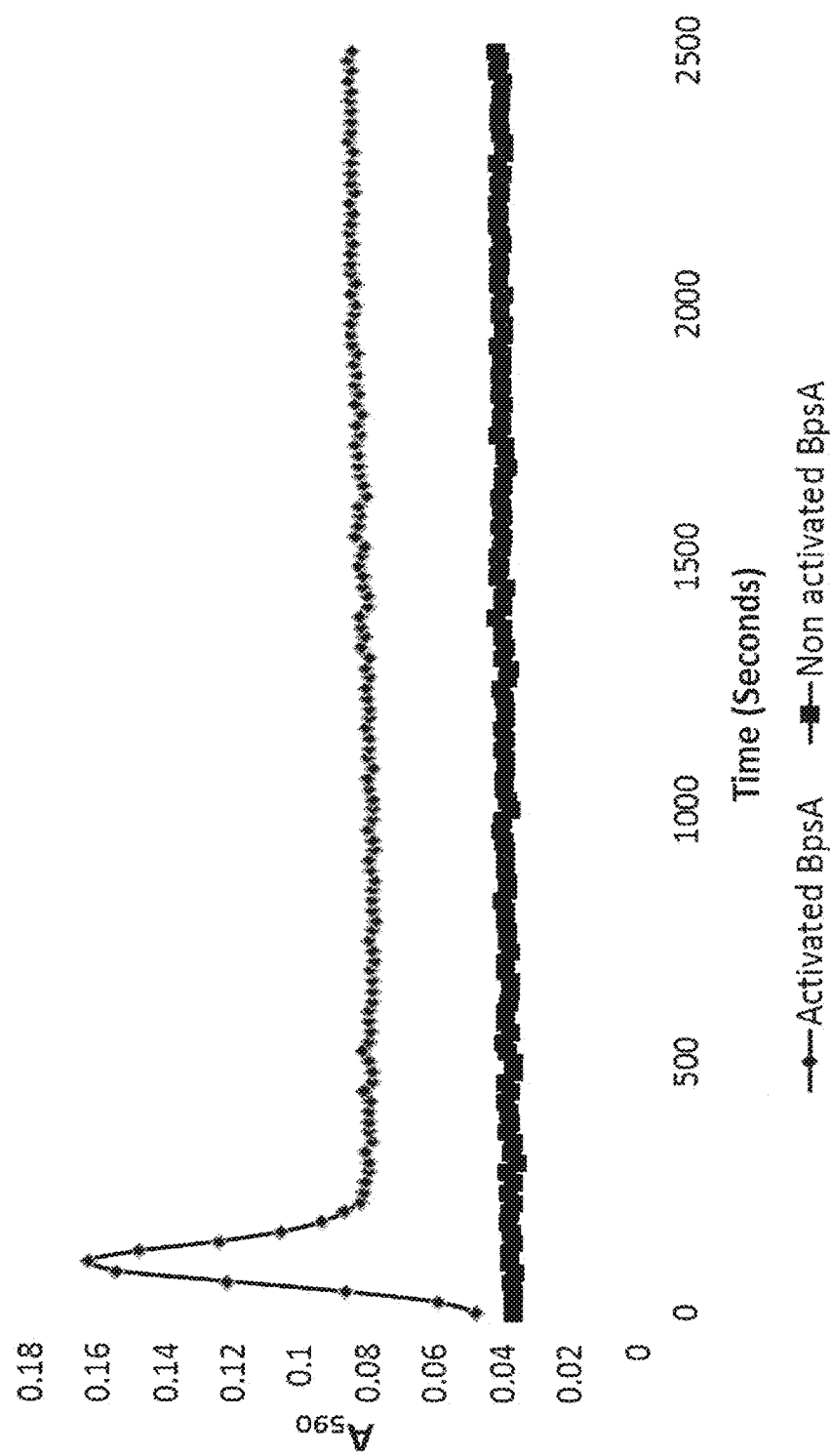
FIG. 1: BpsA activated in vitro, post-purification, by purified Sfp PPTase can synthesise indigoidine. Non-activated BpsA cannot produce indigoidine. Each data point represents the mean of triplicate repeats. The graph displays the first 2500 seconds of the reaction, post-addition of the substrate L-Glutamine.

The following description sets forth numerous exemplary configurations, parameters, and the like. It should be recognised, however, that such description is not intended as a limitation on the scope of the present invention, but is instead provided as a description of exemplary embodiments.

Definitions

In each instance herein, in descriptions, embodiments, and examples of the present invention, the terms "comprising", "including", etc., are to be read expansively, without limitation. Thus, unless the context clearly requires otherwise, throughout the description and the claims, the words "comprise", "comprising", and the like are to be construed in an inclusive sense as to opposed to an exclusive sense, that is to say in the sense of "including but not limited to".

The term "construct", e.g., "genetic construct", refers to a polynucleotide molecule, usually double-stranded DNA, which may have cloned or inserted into it another polynucleotide molecule. For example, a construct may have an unidentified polynucleotide insert that is prepared from an environmental sample or as a cDNA. but not limited thereto. A construct may contain the necessary elements that permit transcription of a cloned or inserted polynucleotide molecule, and, optionally, for translating the transcript into a polypeptide. The inserted polynucleotide molecule may be derived from the host cell, or may be derived from a different cell or organism. Once inside the host cell the construct may become integrated in the host chromosomal DNA. The construct may be linked to a vector.

The term "vector" as used herein refers to a polynucleotide molecule, usually double stranded DNA, which is used to replicate or express a construct. The vector may be used to transport a construct into a given host cell.

The term "polynucleotide(s)," as used herein, means a single or double-stranded deoxyribonucleotide or ribonucleotide polymer of any length, and include as non-limiting examples, coding and non-coding sequences of a gene, genomic DNA, recombinant polynucleotides, isolated and purified naturally occurring DNA or RNA sequences, synthetic RNA and DNA sequences, fragments, constructs, vectors and modified polynucleotides. Reference to nucleic acids, nucleic acid molecules, nucleotide sequences, and polynucleotide sequences is to be similarly understood.

The term "polypeptide", as used herein, encompasses amino add chains of any length, wherein the amino acid residues are linked by covalent peptide bonds. "Polypeptide" may refer to a polypeptide that is a purified natural product, or that has been produced partially or wholly using recombinant or synthetic techniques. The term may refer to an aggregate of a polypeptide such as a dimer or other multimer, a fusion polypeptide, a polypeptide fragment, a polypeptide variant, fragment, or derivative thereof. The term "polypeptide" is used interchangeably herein with the terms "peptide" and "protein". The term, a "polypeptide" may also refer to a "non-ribosomal peptide".

A "fragment" of a polypeptide is a subsequence of a polypeptide. In certain aspects, the fragment is a functional fragment. A functional fragment performs a function that is required for a biological activity or binding and/or provides three dimensional structure of the polypeptide. The term may refer to a polypeptide fragment, an aggregate of a polypeptide fragment, a fusion polypeptide fragment, a fragment of a polypeptide variant, or a fragment of a polypeptide derivative thereof that is capable of performing the polypeptide activity.

The term "full length" as used herein with reference to a wild-type polypeptide sequence means a polypeptide that comprises a contiguous sequence of amino acid residues where each amino acid residue has been expressed from each of its corresponding codons in the polynucleotide over the entire length of the coding region and resulting in a fully functional polypeptide, peptide or protein. As will be appreciated by a person of ordinary skill in the art, a "full length" polypeptide contains the amino acid sequence that corresponds to and has been expressed from each and every codon encoded by the polynucleotide comprising the entire coding region of the polypeptide, wherein each of said codons is located between the start codon and the termination codon normally associated with that coding region.

The term "expressing" refers to the expression of a nucleic acid transcript from a nucleic acid template and/or the translation of that transcript into a polypeptide, and is used herein as commonly used in the art.

The term "incubating" refers to the placing together of elements so they may interact and is used herein as commonly used in the art.

The term "endogenous" as used herein refers to a constituent of a cell, tissue or organism that originates or is produced naturally within that cell, tissue or organism. An "endogenous" constituent may be any constituent including but not limited to a polynucleotide, a polypeptide including a non-ribosomal polypeptide, but not limited thereto.

The term "exogenous" as used herein refers to any constituent of a cell, tissue or organism that does not originate or is not produced naturally within that cell, tissue or organism. An exogenous constituent may be, for example, a polynucleotide sequence that has been introduced into a cell tissue or organism, or a polypeptide expressed in that cell, tissue or organism from that polynucleotide sequence.

"Naturally occurring" as used herein with reference to a polynucleotide sequence according to the invention refers to a primary polynucleotide sequence that is found in nature. A synthetic polynucleotide sequence that is identical to a wild polynucleotide sequence is, for the purposes of this disclosure, considered a naturally occurring sequence. What is important for a naturally occurring polynucleotide sequence is that the actual sequence of nucleotide bases that comprise the polynucleotide is found or known from nature. For example, a wild-type polynucleotide sequence is a naturally occurring polynucleotide sequence, but not limited thereto. A naturally occurring polynucleotide sequence also refers to a variant polynucleotide sequence as found in nature that differs from wild-type. For example, allelic variants and naturally occurring recombinant polynucleotide sequences due to hybridization or horizontal gene transfer, but not limited thereto.

"Non-naturally occurring" as used herein with reference to a polynucleotide sequence according to the invention refers to a polynucleotide sequence that is not found in nature. Examples of non-naturally occurring polynucleotide sequences include artificially produced mutant and variant polynucleotide sequences, made for example by point mutation, insertion, or deletion, but not limited thereto. Non-naturally occurring polynucleotide sequences also include chemically evolved sequences. What is important for a non-naturally occurring polynucleotide sequence according to the invention is that the actual sequence of nucleotide bases that comprise the polynucleotide is not found or known from nature.

The term, "wild-type" when used herein with reference to a polynucleotide refers to a naturally occurring, non-mutant form of a polynucleotide, polypeptide, or organism. A mutant polynucleotide means a polynucleotide that has sustained a mutation as known in the art, such as point mutation, insertion, deletion, substitution, amplification, or translocation, but not limited thereto. A wild-type polypeptide is a polypeptide that is capable of being expressed from a wild-type polynucleotide. In one embodiment, a wild-type polypeptide is a wild-type non-ribosomal peptide that is expressed from a wild-type polynucleotide.

"Homologous" as used herein with reference to polynucleotide regulatory elements, means a polynucleotide regulatory element that is a native and naturally-occurring polynucleotide regulatory element. A homologous polynucleotide regulatory element may be operably linked to a polynucleotide of interest such that the polynucleotide of interest can be expressed from a, vector, construct, or expression cassette according to the invention.

"Heterologous" as used herein with reference to polynucleotide regulatory elements, means a polynucleotide regulatory element that is not a native and naturally-occurring polynucleotide regulatory element. A heterologous polynucleotide regulatory element is not normally associated with the coding sequence to which it is operably linked. A heterologous regulatory element may be operably linked to a polynucleotide of interest such that the polynucleotide of interest can be expressed from a vector, construct, or expression cassette according to the invention. Such promoters may include promoters normally associated with other genes, ORFs or coding regions, and/or promoters isolated from any other bacterial, viral, eukaryotic, or mammalian cell.

"Isolated" as used herein with reference to polynucleotide or polypeptide sequences describes a sequence that has been removed from its natural cellular environment. An isolated molecule may be obtained by any method or combination of methods as known and used in the art, including biochemical, recombinant, and synthetic techniques. The polynucleotide or polypeptide sequences may be prepared by at least one purification step.

"Isolated" when used herein in reference to a cell or host cell describes to a cell or host cell that has been obtained or removed from an organism or from its natural environment and is subsequently maintained in a laboratory environment as known in the art. The term encompasses single cells, per se, as well as cells or host cells comprised in a cell culture and can include a single cell or single host cell.

The term "recombinant" refers to a polynucleotide sequence that is removed from sequences that surround it in its natural context and/or is recombined with sequences that are not present in its natural context. A "recombinant" polypeptide sequence is produced by translation from a "recombinant" polynucleotide sequence.

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues, and orthologues. In certain embodiments, variants of the polypeptides useful in the invention have biological activities that are the same or similar to those of a corresponding wild-type molecule; i.e., functional variants of the parent polypeptide or polynucleotide. In certain embodiments, variants of the polypeptides of the invention have biological activities that differ from their corresponding wild-type molecules. In certain embodiments, the differences are altered activity and/or binding specificity. For example, a functional NRPS variant may produce indigoidine or a related pigment molecule. In certain embodiments, the levels of pigment produced by the functional variant may be higher or lower than produced by the wild-type NRPS.

The term "variant" with reference to polynucleotides and polypeptides encompasses all forms of polynucleotides and polypeptides as defined herein.

As used herein, the term "mutagenesis" refers to methods to alter a polynucleotide sequence either in vitro or in vivo, most commonly to change the sequence of one or more polypeptides encoded therein. Mutagenesis methods include as non-limiting examples, error-prone PCR, DNA shuffling, chemical mutagenesis, application of ultraviolet radiation, genome shuffling, and use of mutator strains. In one application, mutagenesis may be followed by high-throughput screening to enable recovery of improved variants, for example strains of bacteria that as a consequence of mutagenesis now exhibit increased levels of production of glutamine or an analogue thereof.

As used herein, the term in vitro refers to a reaction performed outside of the confines of a living cell or a host organism.

As used herein, the term in vivo refers to a reaction performed within a living cell and/or within a host organism.

The term "high throughput screening" as used herein refers to a significant increase in number of results that can be generated by a given method, in comparison to other methods used to generate the same, or same type of results. For example, methods may be used to screen about 1000 to about 100,000 candidates per day, preferably at least 5,000 candidates per day, preferably at least 10,000 candidates per day, preferably at least 20,000 candidates per day, preferably at least 50,000 candidates per day, preferably at least 100,000 candidates per day, but not limited thereto. Bacterial cultures or extracts from bacterial cultures may be visualised and distinguished by colour; i.e., blue colour indicates that glutamine is being synthesised to form the reporter product, indigoidine or a related pigment molecule. For example, pigment production can be visualised using a spectrophotometer and 96- or 384-well plates as known in the art.

As used herein, the term "analogue", e.g., "glutamine analogue", refers to a modified molecule. In preferred aspect, the analogue retains at least one activity of the unmodified molecule, for example, recognition by a pigment-producing NRPS enzyme, or other biological activity. A glutamine analogue may include one or more additional chemical groups attached to glutamine, and may include conjugate and fusion molecules. Included are peptides, particularly dipeptides, and polypeptides terminating in glutamine. Also included are glutamine analogues that are modified at the amino group attached to the alpha-carbon of glutamine.

Functional glutamine analogues are specifically encompassed by the present invention, i.e., glutamine analogues that retain binding, condensing, or other biological activity. Preferably, the glutamine analogues of the invention can be used to synthesise pigment molecules, particularly pigment molecules related to indigoidine. Exemplary glutamine analogues include alanyl glutamine, glycyl-glutamine and N-trifluoroacetyl-L-glutamine, and also indoleacetyl glutamine, N-acetylglutamine. and phenylacetyl-L-glutamine.

An "indigoidine-related molecule", "indigoidine-related pigment", or similar terminology as used herein refers to pigments that are structurally similar to indigoidine and can be visualised in a manner similar to indigoidine. These coloured compounds are produced using pigment-producing NRPS to condense glutamine analogues as described in detail herein.

"Activation" refers to any enzymatic modification or action that causes the substrate of a given enzyme to adopt a functional conformation or perform a functional role that the substrate was not capable of performing before being activated. For example, a NRPS as described herein may be considered a substrate that is activated by a PPTase. An NRPS is considered "activated" for the purposes of the invention, when it has had a 4'-phosphopantetheine (4'-PP) cofactor attached by a PPTase. Activation of an NRPS means the same thing.

The term "reporter product" as used herein refers to a detectable product formed due to the activity of an activated NRPS.

The term "non-ribosomal peptide synthetase" (NRPS) refers to a biosynthetic enzyme that catalyses the addition of a constituent to a non-ribosomal peptide, for example an amino acid constituent. The term "NKPS" as used herein refers includes a non-ribosomal peptide synthetase that can be activated by a PPTase as described herein. Of particular interest are polypeptides noted herein as "pigment-producing NRPS". These are NRPS polypeptides that produce indigoidine or a related pigment molecule from glutamine or glutamine analogues. Specific NRPS include BpsA, IndC, IgiD, and Plu2187, and polypeptide variants, including modifications and fragments of these polypeptides, as described in detail herein. In preferred embodiments, the NRPS is an enzyme capable of condensing one or more molecules or glutamine or a glutamine analogue into a pigmented product. More preferably, the NRPS is capable of converting two molecules of glutamine or analogues thereof into a pigmented indigoidine or indigoidine-like product.

The term "modified NRPS" (mNRPS) means an NRPS that is not a naturally occurring variant of a wild-type NRPS (wtNRP synthetase). Modified polypeptides useful in the invention may have biological activities that are the same or similar to those of a corresponding wild-type molecule; i.e., a functional modifications of the parent polypeptide or polynucleotide. Alternatively, modified polypeptides of the invention may have biological activities that differ from their corresponding wild-type molecules. In certain embodiments, the differences are altered activity and/or binding specificity. For example, a functional mNRPS may produce indigoidine or a related pigment molecule. In certain embodiments, the levels of pigment produced by the functional modification may be higher or lower than produced by the wild-type NRPS.

The term "non-ribosomal peptide" refers to biologically active small peptides or molecules derived from biologically active small peptides that are synthesised by non-ribosomal peptide synthetases (NRPS) from amino acid precursors wherein the non-ribosomal peptide itself is not directly encoded by a polynucleotide template. A "non-ribosomal peptide" is also a polypeptide as described herein.

The term "PPTase" is used herein as an abbreviation for a phosphopantetheinyl transferase. A PPTase catalyses the attachment of a 4'-phosphopantetheine (4'-PP) cofactor to a non-ribosomal peptide synthetase, or a polyketide synthetase, or a fatty acid synthase. As used herein, "PPTase" encompasses any protein, peptide, and/or polypeptide that can catalyse the attachment of a 4'-phosphopantetheine (4'-PP) cofactor to a non-ribosomal peptide synthetase, or a polyketide synthetase, or a fatty acid synthase. Of particular interest are "NRPS-activating" PPTase. These are PPTase that can activate pigment-producing NRPS to produce indigoidine or a related pigment molecule as described in detail herein. Specific PPTase include PcpS, Sfp, PptT, and PP1183, and polypeptide variants, including modifications and fragments of these polypeptides, as described in detail herein.

As used herein, "a functional PPTase" and "a functional modified PPTase" are a PPTase that can activate an NRPS, namely by catalysing the attachment of a 4'-phosphopantetheine (4'-PP) cofactor as above.

The term "T-domain" refers to the NRPS domain that is the site of attachment of the 4'-PP cofactor, as above. The term T-domain is used interchangeably with peptidyl carrier protein domain (PCP-domain) and carrier protein domain (CP domain).

As used herein, "BpsA protein", "BpsA peptide", and "BpsA polypeptide" mean the same thing and are used interchangeably. Also, according to the inventors' work disclosed herein, and without being bound by theory, due to the unique configuration of BpsA, a BpsA peptide is also an NRPS as used herein, that may be activated by a PPTase.

The terms "BpsA protein", "BpsA peptide" and "BpsA polypeptide" as used herein also refer to: (i) An NRPS that is capable of synthesising indigoidine or a related pigment molecule, (ii) An enzyme capable of synthesising indigoidine or a related pigment molecule, where the enzyme shares at least 70% sequence identity with BpsA from *Streptomyces lavendulae* (DDBJ database accession number AB240063; SEQ ID NO:2), preferably at least 75%, more preferably at least 80%, preferably at least 85%, preferably at least 90%, preferably at least 95%, preferably at least 96%, preferably at least 97%, preferably at least 98%, preferably at least 99%, or preferably 100%, or (iii) An NRPS that contains at least one A-domain, one oxidation domain, one T-domain (also known as a PCP-domain or a CP domain), and one TE-domain, and that is capable of synthesising indigoidine or a related pigment molecule from glutamine or glutamine analogues. The oxidation domain may be located entirely within an A-domain of the NRPS enzyme, as for BpsA from *S. lavendulae*.

The terms "A-domain", "Ox domain", "oxidation domain", "T-domain", "PCP-domain" and "TE-domain" as used herein refer to peptide domains that can be defined as regions of amino acid sequence within NRPS enzymes that contain a majority of the motif sequences for each domain type as defined by Marahiel et al., 1997.

It is intended that reference to a range of numbers disclosed herein (for example, 1 to 10) also incorporates reference to all related numbers within that range (for example, 1, 1.1, 2, 3, 3.9, 4, 5, 6, 6.5, 7, 8, 9 and 10) and also any range of rational numbers within that range (for example 2 to 8, 1.5 to 5.5 and 3.1 to 4.7) and, therefore, all sub-ranges of all ranges expressly disclosed herein are expressly disclosed. These are only examples of what is specifically intended and all possible combinations of numerical values between the lowest value and the highest value enumerated are to be considered to be expressly stated in this application in a similar manner.

Glutamine Levels and Levels of Glutamine Analogues

As noted above, lower levels of glutamine may be associated with fasting or with physical trauma, immune disorders or deficiencies, or cancer. Increased glutamine intake may be used to address muscular cramps or pain, various intestinal conditions, as well as recovery from surgery.

Plasma glutamine levels fall during times of stress such as sepsis, injury, burns, and premature birth. Both high intensity training and endurance training have been shown to reduce the levels of glutamine in the blood. Overtraining (including overtraining syndrome) also reduces glutamine levels.

On the other hand, glutamine levels in the blood plasma are abnormally higher in patients with urea cycle disorders, including N-acetylglutamate synthetase deficiency (NAGSD) and carbamylphosphate synthetase deficiency (CPSD). High levels of glutamine in blood plasma are also seen in ornithine transcarbamylase deficiency (OTCD).

Moreover, very low levels of L-glutamine may be symptomatic of Alzheimer's disease or other neurodegenerative disorders, including frontotemporal lobe dementia and Lewy body disease. Very low levels may also be indicative of certain cancers, particularly carcinomas, such as colorectal cancer. By comparison, very high levels may be symptomatic of aminoaciduria from muscle or tissue breakdown due to range of conditions, such as burns, surgery, wasting diseases, or infection.

In addition, various glutamine analogues are present in urine, and may be used as diagnostic markers. As one example, indoleacetyl glutamine is an indolic derivative of tryptophan;

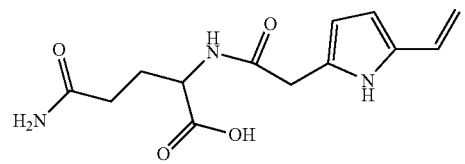 [SMILES: C=Cc1ccc(CC(=O)NC(CCC(N)=O)C(=O)O)[nH]1]

It is generated from indoleacetic acid. Indoleacetic acid (IAA) is a breakdown product of tryptophan metabolism and is often produced by the action of bacteria in the mammalian gut. Some endogenous production of IAA in mammalian tissues also occurs. It may be produced by the decarboxylation of tryptamine or the oxidative deamination of tryptophan. Indoleacetyl glutamine frequently occurs at low levels in urine. Elevated levels have been observed in the urine of patients with Hartnup disease. The characteristic symptoms of this disease are mental retardation and pellagra skin rash.

N-acetylglutamine is an acetylated analogue of glutamine;

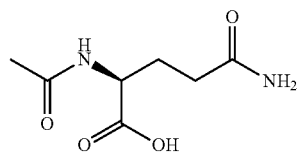

The decomposition products of N-acetylglutamine have been identified by NMR and HPLC-MS as N-acetyl-L-glutamic acid, N-(2,6-dioxo-3-piperidinyl) acetamide, pyroglutamic acid, glutamic acid, and glutamine. N-acetylglutamine is used for parenteral nutrition as a source of glutamine, since glutamine shows much higher instability than N-acetylglutamine. In patients treated with aminoglycosides and/or glycopeptides, elevation of N-acetylglutamine in urine suggests renal tubular injury. High levels of N-acetylated amino acids (i.e., N-acetylglutamine) were detected in a patient with aminoacylase I deficiency (EC 3.5.1.14 enzyme, a homodimeric zinc-binding metalloenzyme). Low levels of N-acetylglutamine may also be associated with autosomal dominant polycystic kidney disease. See, e.g., Gronwald et al., 2011.

Phenylacetylglutamine is a product formed by the conjugation of phenylacetate and glutamine:

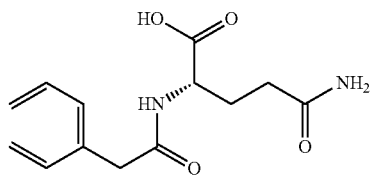 [SMILES: C=C/C=C(\C=C)CC(=O)N[C@@H](CCC(N)=O)C(=O)O]

It is the amino acid acetylation product of phenylacetate (or phenylbutyrate after beta-oxidation). Phenylacetylglutamine is a normal constituent of human urine, but other mammals including dogs, cats, rats, monkeys, sheep and horses do not excrete this compound. Phenylacetyl CoA and glutamine react to form phenylacetyl glutamine and Coenzyme A. The enzyme (glutamine N-acetyl transferase) that catalyses this reaction has been purified from human liver mitochondria and shown to be a distinct polypeptide species from glycine-N-acyltransferase. Phenylacetylglutamine is a major nitrogenous metabolite that accumulates in uremia. See, e.g., Zimmerman et al., 1989; Shockcor et al., 1996.

It has been shown that over 50% of urine phenylacetylglutamine may be derived from kidney conjugation of free plasma phenylacetic acid and/or from the kidney's preferential filtration of conjugated phenylacetic acid. See, e.g., Karoum et al., 1983. Notably, a glutamine N-phenylacetyltransferase (EC 2.3.1.14 enzyme) catalyses the chemical reaction whereby phenylacetyl-CoA is added with L-glutamine CoA and alpha-N-phenylacetyl-L-glutamine Thus, the two substrates of this enzyme are phenylacetyl-CoA and L-glutamine, whereas its two products are CoA and alpha-N-phenylacetyl-L-glutamine. Many disorders that give rise to high urine glutamine also produce high phenylacetyl glutamine.

Accordingly, the invention provides for diagnostic testing, including blood or urine tests, which look to glutamine and/or glutamine analogues in accordance with the present description. The inventors have demonstrated successful testing of blood samples and cell cultures, as described in detail herein. Preliminary experiments have found that testing of urine is also feasible.

NRPS Polypeptides and Polynucleotides

Non-ribosomal peptide synthetases (NRPS) arc enzymes found in many bacteria and fungi, and are known to catalyse the production of biologically active small peptides from amino acid precursors without the need for a nucleic acid template (Finking and Marahiel, 2004; Challis and Naismith, 2004; Marahiel and Essen, 2009). NRPS are very large proteins containing sets of modules, each of which consists of various functional domains such as adenylation (A), condensation (C), cyclization (Cy), thiolation (T), and thioesterase (TE) domains (Marahiel et al., 1997).

NRPS enzymes require activation from an inactive apo to an active holo form by attachment of a 4'-phosphopantetheine (4'-PP) cofactor. This post-translational modification is catalysed by a superfamily of enzymes known as 4'-phosphopantetheinyl transferases (PPTase), which transfer the phosphopantetheinyl group from CoA to a conserved serine residue of their T-domain (Walsh et al., 1997).

One notable NRPS has been identified from *Streptomyces lavendulae* ATCC11924 (Takahashi et al., 2007). The polypeptide, designated as BpsA, is a single module type enzyme containing an oxidation (Ox)-domain (Takahashi et al., 2007). The complete ORF of BpsA consists of 3849 bp (Takahashi et al., 2007; see DDBJ database accession number AB240063; SEQ ID NO:1). A putative ribosome-binding site (RBS). AGGAAG, is located upstream of the strut codon (Takahashi et al., 2007). The BpsA protein consists of 1282 amino acids with a calculated molecular mass of 141 kDa (SEQ ID NO:2).

BpsA consists of a single module comprising four domains (an Adenylation (A-) domain, an oxidation domain, a Thiolation (T-) domain and a Thioesterase (TE-) domain. Collectively, these work to convert two molecules of L-glutamine at a time, via an ATP powered reaction, into a blue pigment that has been identified as water-insoluble 3,3'-bipyridyl, known as indigoidine (Kuhn et al., 1965; Mortimer et al., 1966; Takahashi et al., 2007):

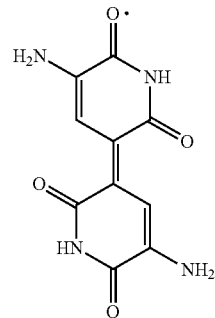

Heterologous expression of BpsA in bacteria has demonstrated that it functions as a synthetase for indigoidine (Takahashi et al., 2007). In vitro assays show that the holotype of BpsA, which is activated by in vitro phosphopantetheinylation, catalyses the synthesis of indigoidine using L-glutamine as a substrate (Takahashi et al., 2007). Thus, BpsA is able to produce indigoidine once it has been converted from inactive precursor (apo-) form to the active (holo-) form by its partner phosphopantheinyl transferase (PPTase) (Takahashi et al., 2007; Owell et al., 2011).

BpsA shares sequence identity with a large number of NRPS (Takahashi et al., 2007). In particular, the protein displays significant amino acid similarity to IndC (Reverchon et al., 2002) (GenBank™ accession number CAB87990) from *Erwinia chrysanthemi* (57% identity) and IgiD (GenBank™ accession number AAD54007) from *Vogesella indigofora* (46% identity) (Takahashi et al., 2007). Other NRPS with sequence similarity include EpoB (GenBank™ accession number AAF62881), EpoP (GenBank™ accession number AAF26925), MtaC (GenBank™ accession number AAF19811), MtaD (GenBank™ accession number AAF19812), and Blm (GenBank™ accession number AAG02365) (Takahashi et al., 2007). All of these proteins show highly conserved amino acid sequences in the Ox domain (Takahashi et al., 2007).

BpsA is a notable as a single NRPS module that (once activated) is capable of synthesising an easy to detect coloured product, without the requirement of additional enzymatic steps (Owell et al., 2011). The inventors have found that BpsA is soluble and expresses well in E. coli as a His6-tagged protein. Due to its comparatively small size, it has been easy to purify using nickel affinity chromatography. The simple structure of BpsA means that it is amenable to directed and rational evolution (Owell et al., 2012). Furthermore, indigoidine is an excellent reporter molecule. It can be detected in vitro and in vivo as it absorbs light strongly at 590 nm. It can also be reduced into a colourless form which is fluorescent and can be detected by flow cytometry (FACS) (Müller et al., 2012; Owell et al., 2011).

To date, all research surrounding BpsA has focused on the production of indigoidine. This has included possible applications of indigoidine as a food colorant or preservative (Takahashi et al., 2007; JP 2007/189969), as a means for assaying PPTase function (Owell et al., 2011; US 2013/026043), as a possible reporter gene to inform on promoter activities in vivo (Müller et al., 2012), and as a reporter gene to detect novel PPTase genes and associated natural product biosynthetic gene dusters from metagenome libraries (Owell et al., 2012; US 2013/026043).

As shown herein, the present inventors have established that pigment-producing NRPS such as BpsA can be used as powerful tools for detecting and measuring glutamine and its analogues. The inventors have carried out in depth studies of BpsA and found that the enzyme is easily purified and very stable. By measuring production of indigoidine, the activated BpsA enzyme (i.e., holotype enzyme activated by a PPTase) can be used to detect L-glutamine concentrations down to micromolar levels. The inventors have found BpsA enzyme to be quite robust, and have determined a good detection range for L-glutamine in complex media, including blood dilutions.

The inventors have also found that the BpsA enzyme can be used to detect and measure a range of glutamine analogues, including alanyl glutamine, glycyl-glutamine, and N-trifluoroacetyl-L-glutamine. In the BpsA enzyme assay of the invention, the glutamine analogues have been used to produce indigoidine-like pigments that can be detected and visualised in a manner similar to indigoidine. Therefore, the inventors consider that various glutamine analogues may be identified and measured with the BpsA enzyme assay. Moreover, these same methods may be adapted to produce indigoidine-related pigments in small or largescale synthesis reactions.

Notably, indigoidine is a radical scavenger and it has been hypothesised that it has a role in protecting S. lavendulae against hydrogen peroxide and superoxide (Takahashi et al., 2007; Müller et al., 2012). The biosynthesis of indigoidine has been also correlated to genetic loci in Erwinia chrysanthemi (indA~indC) (Reverchon et al., 2002), V. indigofera (igiA~igiE) (GenBank™ accession number AF088856), and Photorhabdus luminescens (plu2182, plu2186, and plu2187) (Duchaud et al., 2003), and the indC, igiD, and plu2186 genes in these loci are believed to encode NRPS. Thus, the inventors believe that other NRPS may be used to act as a BpsA enzyme for the synthesis of indigoidine or related pigment molecules.

In this way, the NRPS used in the present invention is not limited to BpsA from Streptomyces lavendulae. Preferably, the NRPS is capable of being recognised and activated via a PPTase. More preferably, the NRPS is a pigment-producing NRPS. In particular embodiments, the NRPS used in the invention may be one of: BpsA; IndC, IgiD, Plu2187, or any of their variants, including modifications or deletions thereof, as described in detail herein.

PPTase Polypeptides and Polynucleotides

As described above, 4'-phosphopantetheinyl transferases (PPTase) catalyse the transfer of a 4'-phosphopantetheine moiety from coenzyme A to phosphopantetheine-dependent carrier proteins. In primary bacterial metabolism, PPTase are essential for viability, as activated acyl carrier proteins are involved in fatty acid biosynthesis. In secondary metabolism, PPTase serve to activate the carrier protein domains (CP-domains, also referred to as T-domains) of NRPS enzymes, which are often implicated in the synthesis of virulence factors in bacteria and fungi.

Several PPTase enzymes have been identified with narrow substrate specificity, including AcpS from Bacillus subtilis and Escherichia coli (Gehring et al., 1997; Mootz et al., 2001) and PcpS from the pathogenic bacterium Pseudomonas aeruginosa (Finking et al., 2002; Seidle et al., 2006). PPTase enzymes with broad substrate specificity have also been identified, including Sfp from Bacillus subtilis (Quadri et al., 1998) and Svc from Streptomyces verticillus (Sanchez et al., 2001). In addition, humans have a single PPTase that serves to activate acyl carrier proteins for fatty acid synthesis (Joshi et al., 2003).

As noted above and shown herein, the present inventors have found that pigment-producing NRPS such as BpsA are useful biodetectors for identifying and measuring glutamine and its analogues, where NRPS activation is mediated by a PPTase. In accordance with the present invention, the PPTase may be any PPTase. Preferably, the PPTase is capable of recognising and activating the T-domain of BpsA or another NRPS enzyme. In certain embodiments, the PPTase may be modified to alter its substrate specificity. Alternatively, the NRPS may be modified by swapping T-domains and evolving the resulting polypeptide to produce a substrate for any PPTase.

In particular embodiments, the PPTase used in the invention may be one of: PcpS from Pseudomonas aeruginosa; Sfp from B. subtilis subsp. spizizenii ATCC6633, PptT from Mycobacterium tuberculosis (Chalut et al., 2006), the putative PPTase PP1183 of P. putida KT2440, or any of their variants, including modifications or deletions thereof, as described in detail herein.

Related Polynucleotide and Polypeptide Sequences

In addition to the sequences noted herein, the methods of the invention may be used with related polypeptide and polynucleotide sequences. In one embodiment, the invention utilises fragments or variants of NRPS polynucleotides and polypeptides, for example, fragments or variants of BpsA or other pigment-producing NRPS as described herein. Fragments and variants of SEQ ID NO:1 and SEQ ID NO:2 are specifically encompassed by the present invention. The invention may also utilise PPTase fragments or variants, for example, fragments or variants of PcpS or PptT, or any other PPTase as described herein.

According to the invention, a fragment of a polynucleotide sequence includes a subsequence of contiguous nucleotides. Preferably, the polynucleotide fragment allows expression of at least a portion of an NRPS or PPTase, e.g., expression of one or more functional domain of the polypeptide.

A fragment of a polypeptide disclosed herein includes a subsequence of contiguous amino acids of the polypeptide. Preferably the polypeptide fragment is a functional fragment. i.e., a fragment capable of binding or other biological activity. For example, an NRPS polypeptide fragment may be capable of producing the pigment indigoidine or a related pigment molecule. A PPTase polypeptide fragment may be capable of activating one or more NRPS.

In a particular embodiment, the polypeptide fragment may include at least one functional domain. For example, for an NRPS polypeptide, a fragment would include one or more of a T-domain (also known as a PCP-domain or CP-domain). For a PPTase polypeptide, a fragment would include one or more domains that interact with a NRPS polypeptide and/or coenzyme A.

According to the invention, variant polynucleotides include polynucleotides that differ from the disclosed sequences but that as a consequence of the degeneracy of the genetic code, encode a polypeptide having similar activity to a polypeptide encoded by a disclosed polynucleotide. A sequence alteration that does not change the amino acid sequence of the polypeptide is termed a silent variation. Except for ATG (methionine) and TGG (tryptophan), other codons for the same amino acid may be changed by art recognised techniques, e.g., to optimise codon expression in a particular host organism.

Variant polynucleotide sequences preferably exhibit at least 50%, at least 60%, preferably at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, and preferably at least 99% identity to a sequence of the present disclosure.

Identity may be found over a comparison window of at least 1500 nucleotide positions, preferably at least 2000 nucleotide positions, preferably at least 2500 nucleotide positions, preferably at least 3000 nucleotide positions, preferably at least 3500 nucleotide positions. preferably at least 3800 nucleotide positions and most preferably over the entire length of a polynucleotide used according to a method of the invention.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990).

Polynucleotide sequence identity and similarity can be determined in the following manner. The subject polynucleotide sequence is compared to a candidate polynucleotide sequence using sequence alignment algorithms and sequence similarity search tools such as in GenBank, EMBL, Swiss-PROT and other databases. Nucleic Acids Res 29:1-10 and 11-16, 2001 provides examples of onlineresources.

As to polypeptide variants, an amino acid sequence may differ from a polypeptide disclosed herein by one or more conservative amino acid substitutions, deletions, additions or insertions which do not affect the biological activity of the peptide. Conservative substitutions typically include the substitution of one amino acid for another with similar characteristics, e.g., substitutions within the following groups: glycine, alanine; valine, isoleucine, leucine; aspartic acid, glutamic acid; asparagine, glutamine; serine, threonine; lysine, arginine; and phenylalanine, tyrosine. Non-conservative substitutions will entail exchanging a member of one of these classes for a member of another class.

Other variants include peptides with modifications which influence peptide stability. Such analogues may contain, for example, one or more non-peptide bonds (which replace the peptide bonds) in the peptide sequence. Also included are analogues that include residues other than naturally occurring L-amino acids, e.g. D-amino acids or non-naturally occurring synthetic amino acids, e.g. beta or gamma amino acids and cyclic analogues.

Substitutions, deletions, additions, or insertions may be made by mutagenesis methods known in the art. A skilled worker will be aware of methods for making phenotypically silent amino acid substitutions. See, for example, Bowie et al., 1990. A polypeptide may be modified during or after synthesis, for example, by biotinylation, benzylation, glycosylation, phosphorylation, amidation, by derivatisation using blocking/protecting groups and the like. Such modifications may increase stability or activity of the polypeptide.

Polypeptide variants encompass naturally occurring, recombinantly and synthetically produced polypeptides. Variant polypeptide sequences preferably exhibit at least 50%, preferably at least 60%, preferably at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, and preferably at least 99% identity to a sequence of the present disclosure.

Identity may be found over a comparison window of at least 600 amino add positions, preferably at least 700 amino add positions, preferably at least 800 amino acid positions, preferably at least 900 amino acid positions, preferably at least 1000 amino acid positions, preferably at least 1100 amino acid positions, preferably at least 1200 amino acid positions, and most preferably over the entire length of a polypeptide used in or identified according to a method of the invention. Polypeptide variants also encompass those that exhibit a similarity to one or more of the specifically identified sequences that is likely to preserve the functional equivalence of those sequences and which could not reasonably he expected to have occurred by random chance.

In preferred embodiments, the polypeptide variant is a functional variant, i.e., a variant capable of binding or other biological activity. For example, an NRPS polypeptide variant may be capable of producing the pigment indigoidine or a related pigment molecule. A PPTase polypeptide variant may be capable of activating one or more NRPS as described in detail herein.

Expression of NRPS and PPTase Polypeptides

In one embodiment of the invention, the NRPS and/or PPTase polypeptide is expressed using a nucleic acid construct. For example, an NRPS construct may be used, i.e., a nucleic acid expression construct that comprises a polynucleotide sequence that encodes an NRPS operatively linked to a promoter that allows expression of the polynucleotide sequence to form the NRPS. The PPTase polypeptide may be expressed in a similar manner. Preferably, the NRPS is a pigment-producing NRPS, for example, BpsA or a functional variant thereof. Preferably, the PPTase is an NRPS-activating enzyme, for example, PcpS or PptT, or any functional variant thereof.

An expression cassette may be used to include the necessary elements that permit the transcription of a polynucleotide molecule that has been cloned or inserted into the construct. Optionally, the expression cassette may comprise some or all of the necessary elements for translating the transcript produced from the expression cassette into a polypeptide. An expression cassette may include NRPS and/or PPTase coding regions. It may also include any necessary noncoding regions.

The NRPS construct may be a construct for expression of BpsA or other pigment-producing NRPS, or any functional variants thereof. The construct may be a nucleic acid expression construct comprising a polynucleotide sequence encoding the pigment-producing polypeptide operatively linked to a promoter that allows expression of the polynucleotide sequence.

In order for pigment synthesis to occur, the NRPS polypeptide or its functional variant must first be activated by a PPTase. Typically, this occurs by post-translational attachment of a 4'-PP group to the active site serine of the T-domain. As described above, the activation of BpsA is catalysed by a cognate PPTase enzyme, which is able to recognise specific sequence elements in the T-domain of BpsA. The naturally occurring PPTase enzymes of some bacteria such as *E. coli* may be unable to fulfil this role effectively.

In accordance with the present invention, the activation of the NRPS polypeptide or its functional variant can be carried out prior to or following isolation of the NRPS polypeptide or its functional variant, i.e., pre-isolation activation or post-isolation activation, as described in detail herein. in addition, the NRPS polypeptide or its functional variant may be activated in vitro prior to incubation with a test sample, or the NRPS polypeptide or its functional variant may be activated in vivo and isolated prior to incubation with a test sample.

Therefore, in specific embodiments, it may be useful to carry out co-incubation or co-expression of an activating PPTase enzyme with the NRPS polypeptide or its functional variant in order for activation to a form capable of pigment synthesis to occur. For example, co-incubation can be carried out in vitro, while co-expression can be carried out in vivo. In one specific embodiment, the NRPS polypeptide or its functional variant may be isolated and then incubated with an isolated PPTase enzyme to enable attachment of a 4'-PP group to occur. In another embodiment, the NRPS and PPTase genes may be expressed in the same organism, so that upon purification the NRPS protein will already have a 4'-PP group attached. Similar approaches may be used for BpsA and other pigment-producing NRPS, and any functional variants thereof.

The polynucleotide sequence encoding the NRPS may be any suitable NRPS polynucleotide sequence from any organism. Preferably the organism is a bacterial cell or strain; alternatively, a eukaryotic cell or cell line may be used. In one non-limiting embodiment, the polynucleotide sequence encoding BpsA or other pigment-producing NRPS, or functional variants thereof, may be any naturally occurring polynucleotide sequence from any bacterial cell or strain.

The polynucleotide sequence encoding the NRPS may be a naturally occurring (i.e., wild-type) or modified polynucleotide sequence. For example, the wild-type or modified sequence of BpsA from *Streptomyces lavendulae* may be used. Alternatively, the polynucleotide sequence encoding the NRPS may be a wild-type or modified polynucleotide sequence from *Erwinia chrysanthemum*, *Vogesella indigofera*, or *Photorhabdus luminescens*, as described herein. In the same way, the PPTase polynucleotide may be a wild-type or modified sequence.

In one embodiment, a construct is made by cloning a polynucleotide sequence encoding a wild-type or modified polypeptide as above into an appropriate vector. An appropriate vector is any vector that comprises a promoter operatively linked to the cloned, inserted polynucleotide sequence that allows expression of the polypeptide from the vector. A skilled worker appreciates that different vectors may be employed in the methods of the invention. In addition methods for constructing vectors, including the choice of an appropriate vector, and the cloning and expression of a polynucleotide sequence inserted into an appropriate vector as described above is believed to be within the capabilities of a person of skill in the art (Sambrook et al., 2003).

Preferably, the expressed NRPS is BpsA or a functional variant thereof. Expression may be inducible, for example, with IPTG. Similar approaches may be used for other pigment-producing NRPS and any functional variants thereof. In the same way, expression of the PPTase may be inducible. The person of skill in the art recognises that there are also many suitable alternative expression systems available that may be used in the methods of the invention to express an NRPS and/or PPTase polypeptide.

Preferably, expression is in a suitable host cell or strain. In one embodiment, the host cell or strain may be a cell or strain of *E. coli*. Alternatively, the expression vector is chosen to allow inducible expression in a non-*E. coli* host cell or strain. Expression may also be obtained using in vitro expression systems; such systems are well known in the art.

In one embodiment, the NRPS and PPTase are co-expressed in the same host cell or strain. To achieve dual expression within the same host cell or strain, the nucleotide sequence encoding the PPTase and the NRPS may be cloned into suitable, separate expression vectors. Suitable vectors may have the same or compatible origins of replication in order to be stably maintained in the same host cell or strain. Preferably, the NRPS construct encodes BpsA or a functional variant thereof. Also preferred, the PPTase construct encodes PcpS or PptT, or any functional variant thereof.

In another embodiment, polynucleotide sequences encoding NRPS may be integrated into the chromosome of an appropriate host organism as described herein, to produce a strain useful in the invention. In one embodiment, an NRPS construct comprises a nucleotide sequence encoding a NRPS polypeptide and a suitable regulatory promoter that is integrated into the chromosome of *E. coli* or other host organism in an appropriate orientation to allow expression of the polypeptide in the cell. A similar approach may be used for integration of PPTase polynucleotide sequences.

In one particular embodiment, both an NRPS and a PPTase are integrated into a host cell. For example, a PPTase construct and a NRPS construct may both be integrated and then expressed in vivo. The constructs may allow co-expression of wild-type polypeptides or functional variants.

Thus, in a specific embodiment, a PcpS (or PptT) construct and a BpsA construct are expressed in the same host cell or strain.

In specific embodiments of the invention, the expressed NRPS and PPTase polypeptides may be isolated using various biochemical techniques. These techniques include but are not limited to filtration, centrifugation, and various types of chromatography, such as ion-exchange, affinity, hydrophobic interaction, size exclusion, and reverse-phase chromatography. In one particular embodiment, Ni-NTA affinity chromatography is used.

In certain embodiments, the polypeptides may be linked to a solid substrate such as beads, filters, fibers, paper, membranes, chips, and plates such as multiwell plates. The polypeptides may also be prepared as a polypeptide conjugates in accordance with known methods.

Host Cells and Strains

The expression of an NRPS or PPTase polypeptide may be carried out in vitro or in vivo. In vivo expression may be carried out in a suitable host cell or strain. According to this embodiment, a suitable host cell or strain may be any suitable prokaryotic or eukaryotic cell in which the NRPS may be expressed wherein the NRPS is not activated in the cell by any endogenous activity of the cell.

In one embodiment, a suitable host cell or strain may be any suitable prokaryotic or eukaryotic cell in which BpsA or other pigment-producing NRPS, or any functional variants thereof, may be expressed. In a particular embodiment the polypeptide is not activated by any endogenous activity of said cell. The suitable host cell or strain may be a bacterial cell or strain. In particular embodiments, eukaryotic cells or strains may be used.

Introduction of an NRPS and/or PPTase construct into an appropriate host cell or strain may be achieved using any of a number of available standard protocols and/or as described herein as known and used in the art (Sambrook et al., 2003). Preferably, the NRPS construct is a BpsA construct as described herein. Preferably, the construct is inserted into an appropriate host cell or strain. Such insertion may be achieved using any of a number of available standard transformation or transduction protocols as known and used in the art (Sambrook et al., 2003).

In certain embodiments, the host cell or strain expresses an NRPS that can be activated by a PPTase. In one embodiment, the host cell or strain is a fungal or bacterial, preferably bacterial, host cell or strain, but not limited thereto. Preferably, the bacterial cell or strain is a Gram negative bacterial cell or strain. Preferably, the bacterial cell or strain is a cell or strain of *E. coli*. For industrial applications, the host strain may be *Brevibacterium* flavin, *Flavobacterium rigense*, or *Corynebacterium glutamicum*, or any functional variant thereof.

In one embodiment, the expressed polypeptide (e.g., NRPS and/or PPTase) is an exogenous polypeptide in the host cell or strain expressed from a construct according to the invention, but not limited thereto. Alternatively, the polypeptide is expressed from the genome of the host cell or strain. In this embodiment, the polypeptide may be endogenous $_{OT}$ exogenous, naturally occurring or non-naturally occurring with respect of the host cell or strain. In one particular embodiment, a single host organism could be modified to allow expression of multiple NRPS polypeptides in the cell, including modified NRPS to maximise the detection of glutamine and its analogues.

By way of non-limiting example, the NRPS may be an exogenous polypeptide expressed from an NRPS expression construct. Preferably the NRPS so expressed is a BpsA polypeptide or a functional variant thereof. In this embodiment, the NRPS is an endogenous NRPS that synthesises a pigment or dye. Preferably, the pigment or dye is indigoidine or a related pigment molecule.

Host cells and strains useful in the invention are not limited to strains of *E. coli* or the other strains described herein. Numerous alternative host organisms may be useful in the methods according to the invention, wherein each cell or strain may provide a different or additional benefit or utility. The choice of an appropriate host strain will affect choice of construct used based on the genetic makeup of the host.

A key reason for using different host strains is that not all proteins can be expressed effectively in some strains (e.g., *E. coli* strains) due to promoter inactivity, codon bias, protein insolubility, or other factors. Therefore, the use of different host strains provides alternative hosts suitable for use in production of any polypeptide disclosed herein.

Detection and Measurement of Glutamine and its Analogues

In various embodiments, the invention relates to in vitro and in vivo methods for detection and quantification of pigment synthesis by an NRPS. In this way, the NRPS is used as an effective biodetector. In particular embodiments, the invention relates to methods of using BpsA or other pigment-producing NRPS, or any functional variants thereof, for the detection of glutamine or its analogues. These methods allow the presence and relative levels of glutamine or glutamine analogues to be determined. Such methods find use in both medical and research settings. In certain embodiments, the methods of the invention are carried out using kits as described in detail herein.

In certain embodiments, the present invention relates to the use of NRPS such as BpsA, or other pigment-producing NRPS, or any functional variants thereof in colorimetric assays. This colorimetric analysis can be performed to determine the presence and/or amount of Glutamine or analogue thereof in a sample. The glutamine or glutamine analogue can be a natural compound, such as one that is produced by an organism, or can be a non-natural compound, such as a synthetic compound.

According to the present invention, the activation of the NRPS polypeptide or its functional variant can be carried out prior to or following isolation of the NRPS polypeptide or its functional variant, i.e., pre-isolation activation or post-isolation activation, as described in detail herein. Additionally, the NRPS polypeptide or its functional variant may be activated in vitro prior to incubation with a test sample, or the NRPS polypeptide or its functional variant may be activated in vivo and isolated prior to incubation with a test sample.

As outlined above, the NRPS enzyme used in the methods of the invention may be expressed in and isolated from a host strains that also expresses an activating PPTase. In this scenario, the NRPS enzyme will be activated to a holo form in vivo, prior to isolation. Alternatively, the apo (inactive) form of an NRPS may be isolated and then incubated with an isolated PPTase in vitro, thereby activating the NRPS to its holo form. It will be understood that other approaches may also be used to obtain the NRPS and PPTase enzymes used in the invention. The invention is not limited to a particular approach for producing, isolating, or activating the enzymes that are used.

The methods of the invention may be performed in a water-based solution, such as a buffered aqueous solution. In some embodiments, the NRPS and PPTase enzymes can be included separately or can be pre-mixed according to the methods of the invention. For example, kits and methods of the invention can include separate NRPS and PPTase enzymes or a mixture of these enzymes. In other embodiments, the kits and methods of the invention can also include a glutamine-based substrate (or the indigoidine reaction product, or a related pigment molecule) as controls.

The NRPS and/or PPTase enzymes of the invention can be provided in solid or liquid form, depending on the desired arrangement of the kit or composition. If the enzyme is a liquid at ambient conditions, it may be diluted with a suitable solvent, such as water. Alternatively, the enzyme may be supplied in a dry form (e.g., powder, granule, pellet, etc.) and then be dissolved prior to use by using an appropriate solvent.

As understood in the art, a colorimetric analysis or colorimetric assay may be conducted using specialised equipment to quantify and measure the wavelength and/or absorbance of the solution being analysed. Such equipment includes, but is not limited to UV-visible spectrophotometers and multiwell plate readers. In certain embodiments, colorimetric analysis and measurement of the pigment product may be carried out at 590 nm. In some embodiments, the colorimetric analysis or colorimetric assay may be conducted using the unaided human eye.

The sample including glutamine or a glutamine analogue to be detected can be a biological or a non-biological sample. A biological sample can be any material taken from an organism such as body fluid from a mammal, material derived from an organism, or a sample that has organisms in it. Biological samples may include certain tissues, for example, tumour tissue or nervous tissue, or body fluid such as blood, urine, sputum, saliva, mucus, vitreal fluid, synovial fluid, semen, cerebrospinal fluid, lymph fluid, bone marrow, amniotic fluid, bile, lacrimal fluid, perspiration, etc. Exemplary biological samples include blood samples (e.g., blood serum or plasma), urine samples, saliva samples, cerebrospinal fluid samples, lymph fluid samples, eukaryotic cell culture samples, and bacterial cell culture samples.

Biological samples can be obtained from patients and analysed for the levels of glutamine associated with health conditions or disease states, as detailed further below. Assessment of glutamine levels can be used to determine the absence, presence, or degree of a health condition or disease state. Levels of glutamine can be assessed during or following medical treatment to determine whether such treatment has been successful. Biological samples can also include sections of tissues such as frozen sections taken for histological purposes, which can also be analysed for glutamine or glutamine analogues.

Other samples, including biological samples, can be those derived from fermentation, cell culturing, and amino acid production. If the sample is initially complex, solid, or viscous, it can optionally be treated, such as by extraction, or it can be dissolved or diluted in order to obtain a sample having the appropriate characteristics for use in the colour based assay. Non-biological samples may also be used, e.g., a composition of a chemically-synthesised component.

The detection and measurement methods of the invention may be performed in any suitable assay vessels. This includes any suitable receptacle in which glutamine or glutamine analogue detection and measurement can be performed. The assay vessel can be made from material such as glass (e.g., surface modified glass), quartz, or plastic, such as polystyrene, polypropylene, and polycarbonate. Useful assay vessels include single and multi-well plates, e.g., 6, 24, 96, 384, and 1536 well plates. These are commonly referred to as microliter plates, microplates, or microwell plates. Depending on the type of plate used, each well can hold from microliter to milliliter volumes of liquid. Other types of assay vessels that can be used include capillary tubes and Eppendorf tubes. The assay vessel can optionally be included in a kit, or can be supplied by the user to carry out the methods as described herein.

The kits and methods of the invention can be used with the enzymes provided in solution or linked to a solid phase. The invention is not limited to any type of assay formal, but some examples are discussed to illustrate aspects of the invention. The particular format employed will depend on the particular goal to be achieved, e.g., diagnostic assays or bacterial screening assays.

Kits of the invention can include one or more components, for example one or more NRPS, useful for performing the detection or measurement methods described herein. The kit can include optional components such as PPTase enzymes to activate the NRPS, and enzyme substrates such as glutamine or glutamine analogues. The kit can also include vessels, such as tubes or multi-welled plates, in which the chromogenic reaction can take place and be analysed. The kit can also include a solubility-enhancing component.

A biological sample that includes glutamine or a glutamine analogue can be placed in an analysis vessel, such as a well in a multiwall plate, so the glutamine or glutamine analogue can be detected using methods of the invention. Typically, steps for these methods can be performed using a suitable solution(s), including incubation buffers, reaction buffers, washing buffers, and blocking buffers. The solution can be an aqueous buffered solution, and preferably maintains enzyme configuration for proper binding and enzymatic activities. A blocking solution can also be used to block non-specific adherence to vessel binding sites. Preferably, the reaction buffer comprises a Tris solution (e.g., Tris-HCl) to maintain pH between 7-9.2, more preferably at about pH 8. In another preferred embodiment, ATP is added to the reaction buffer.

When included in aqueous solutions, the enzymes used in the invention (e.g., NRPS, and optionally a PPTase) can optionally be formulated to include water soluble co-solvents to increase solubility. Examples of useful optional co-solvents are alcohols (e.g., methanol, ethanol, propanol), polyalcohols (e.g., glycerol, propylene glycol), dimethylsulfoxide, dimethylformamide, acetonitrile, and similar solvents. Solvents are widely used for in vitro diagnostic applications, and can be readily selected by a person of skill in the art.

In one embodiment, an analysis vessel (such as a multi-well plate) is provided that has an NRPS enzyme immobilised on a solid surface of the vessel. The enzyme can be immobilized directly to the vessel surface or by its conjugation to a binding member, with the binding member directly or indirectly bound to the vessel surface. In alternative embodiments, the enzyme is immobilised to other solid surfaces, such as one or more beads, filters, fibers, paper, membranes, and chips.

The glutamine and/or glutamine analogues can be present in a test solution, which can be added to a reaction vessel that includes the NRPS enzyme. The reaction solution can be prepared from components of a kit that include the NRPS enzyme, reaction buffer, and optionally, the PPTase enzyme. In some embodiments, the two enzymes are supplied in a ready-to-use one component composition or solution. In other embodiments the enzymes are provided to a user separately, in a kit. The kit can optionally include one or more different liquids, such as dimethylsulfoxide (DMSO), where dissolution of the chromogenic pigment would be facilitated using such components. Alternatively, DMSO may be substituted with other solvents, such as DMF (dimethyl formamide).

Optionally, a co-solvent can be included in the reaction composition with the NRPS enzyme. The co-solvent can ensure the reagents of the reaction composition be maintained in soluble form and do not precipitate out of solution during the reaction, or later, such as upon addition of the stop reagent. Exemplary co-solvents include alcohols (e.g., methanol, ethanol, propanol), polyalcohols (e.g., glycerol, propylene glycol), dimethylsulfoxide, dimethylformamide, acetonitrile, and similar agents.

In some embodiments, the reaction solution that includes the components sufficient for colour development can then be added directly to the vessel that includes the NRPS enzyme. Alternatively, components of the kit can be mixed directly in the weHs. Using multiwall plates, the reaction solution can be dispensed, for example, by pipetting, in the well manually or using automated apparatus. Multi-tip pipetting apparatus can be used to increase the speed of the dispensing and or mixing process. Using a 96-well plate format, typical reaction volumes range from about 25 pL to about 200 pL, or from about 50 tL to about 150 tL.

The NRPS reaction resulting in the conversion of the glutamine or glutamine analogue substrate into the chromogenic pigment can be carried out for a desired period of time at a desired temperature. The reaction can be monitored visually or spectrophotometrically to determine the development of colour in the composition. The incubation step will typically occur at room temperature, although a temperature in the range of about 10° C. to about 50° C. can be employed. Incubation times will typically range from about 1 to about 60 minutes, or more usually about 5 to about 45 minutes. In some cases the pH of the reaction composition is in the range of about 7.0 to about 8.5, or more specifically in the range of about 7.9 to about 8.2. Preferably the pH is about 8.0.

In particular embodiments, the absorbance of the chromogenic pigment as determined by a spectrophotometric method will be directly proportional to the amount of glutamine or glutamine analogue in the sample. For quantitation, absorbance can be accurately measured using appropriate hardware and software if desired. Controls can be employed, where the signal to concentration of the glutamine or glutamine analogue is determined, so that the signal can be directly related to the concentration of glutamine or glutamine analogue in the assayed sample. Alternatively, the measured glutamine or glutamine analogue levels can be compared to standard levels that have been previously calculated, e.g., normal or expected levels. Accordingly, both the presence and the amount of glutamine or glutamine analogue in the sample can be determined.

Simple spectrophotometers, such as UV/VIS spectrophotometers for wavelengths between 175 nm and 900 nm capable of determining the absorbance of a sample are commercially available, for example, from Perkin Elmer. In analysing the sample, a light of a specific wavelength, such as selected by an optical filter or monochromator, is transmitted through the sample, and a detector measures the percentage of the initial transmitted through the sample. The amount of transmitted light is generally inversely proportional to the amount of pigment in the sample. Alternatively, analysis may be performed using a microplate reader. A variety of microplate readers capable of accommodating and analysing the absorbance of samples in the wells of 96-well plates, are commercially available, from, for example BioTek (Winooski, Vt.).

In one other embodiment, the methods of the invention are used for measurement of glutamine for diagnosis. As noted above, altered glutamine levels are associated with various health conditions and disease states.

Glutamine levels fall during times of stress such as sepsis, injury, burns, and premature birth. High intensity training, endurance training, and overtraining have been shown to reduce levels of glutamine. Very low levels of glutamine may be seen with Alzheimer's disease or other neurodegenerative disorders, including frontotemporal lobe dementia or Lewy body disease. Lower levels of glutamine may be associated with fasting or with physical trauma, immune disorders or deficiencies, or cancer, particularly carcinomas, such as colorectal cancer. Glutamine supplementation may be used to address muscular cramps or pain, various intestinal conditions, as well as recovery from surgery.

Conversely, glutamine levels are higher than normal in patients with urea cycle disorders. Specific deficiencies in urea cycle disorders include N-acetyl glutamate synthetase deficiency, carbamoylphosphate synthetase I deficiency, ornithine transcarbamylase deficiency, citrullinemia type I deficiency, argininosuccinic aciduria, and arginase deficiency (hyperargininemia). Very high levels of glutamine may be seen with aminoaciduria from muscle or tissue breakdown due to range of conditions, such as burns, surgery, wasting diseases, and infection.

In addition, levels of indoleacetyl glutamine are elevated in patients with Hartnup disease. Higher levels of N-acetylglutamine may be seen in patients with renal tubal injury and aminoacylase deficiency. Lower levels of N-acetylglutamine are found in association with autosomal dominant polycystic kidney disease. Increased levels of phenylacetyl-L-glutamine are associated with uremia.

Thus, the method of the invention may employ an NRPS enzyme for detecting increased or decreased glutamine or glutamine analogue levels in a subject, where such levels are indicative of a health condition or disease state. In one embodiment, the method comprises providing a biological sample from the subject that may contain excessive or deficient levels of glutamine or glutamine analogue. A test reaction is further provided by contacting the biological sample with a NRPS enzyme to produce indigoidine or a related pigment molecule. In this way, the enzyme modifies the endogenous glutamine or glutamine analogue from the subject. Modification produces a coloured pigment as described herein. Data from a control reaction comprising the enzyme and set concentration of glutamine or glutamine analogue, or the enzyme and a biological sample from a healthy subject, is also provided. The pigment produced by the test reaction is detected. The presence of the health condition or disease state is indicated by a difference of glutamine or glutamine analogue levels in the test reaction and the glutamine or glutamine analogue levels in the control reaction.

Without wishing to be bound by theory, it is believed that BpsA or a related enzyme can be used to measure both L-glutamine and a glutamine analogue (e.g., L-glycyl glutamine) in the same sample. Experiments have shown that L-glutamine reacts much faster with BpsA (~100-1000 fold) than an analogue. Thus, it would be possible to incubate the sample for a short period (e.g., 2 minutes), remove the blue pigment, and measure the pigment levels to calculate L-glutamine levels. It would then be possible to wait for a further longer period (e.g., 8 hours), and measure the remaining blue pigment to calculate analogue levels (e.g., L-glycyl glutamine). It is expected that there would be little contamination of the glutamine-based product by the analogue-based product based on the enzymatic profile for BpsA.

In one further embodiment, the methods of the invention are used to measure glutamine or glutamine analogue production by an industrial strain of bacteria. As noted above, various bacterial strains are used to make glutamine to be sold as a fine chemical. Using the assays set out herein, it would be possible to monitor glutamine or glutamine analogue production by the producer strain. It would be possible also to mutate the producer strain and select for mutants that make more glutamine or glutamine analogue.

Thus, the method of the invention may employ an NRPS enzyme for detecting altered glutamine or glutamine analogue levels in a bacterial cell. In one embodiment, the method comprises incubating a bacterial cell or strain (i.e., test cell or strain) expressing an NRPS enzyme under conditions to produce indigoidine or a related pigment molecule. The NRPS may be activated by a PPTase that is co-expressed by the bacterial cell or strain. Alternatively, the NRPS may be activated by incubation of the bacterial cell or strain with a PPTase.

The activated NRPS enzyme may then modify the glutamine or glutamine analogue synthesised by the bacteria. Modification of the glutamine or glutamine analogue produces a coloured pigment which can be visualised as blue bacterial cultures. A control comprising bacteria with standard or starting glutamine or glutamine analogue levels (i.e., control cell or strain) may also be provided. Defective or enhanced production is indicated by a difference of glutamine or glutamine analogue levels in the test cultures and the glutamine or glutamine analogue levels in the control cultures.

In an alternative embodiment, the bacterial cell or strain (i.e., test cell or strain) is incubated with an exogenously added NRPS enzyme under conditions to produce indigoidine or a related pigment molecule. The NRPS may be pre-activated by the PPTase prior to incubation with the bacterial cell or strain. The coloured pigment can be then measured in solution. In certain embodiments, high-throughput screening may be used to screen large numbers of bacterial cells. Similar approaches may be used to identify a bacterial cell or strain that produces increased levels of a glutamine analogue.

It should be noted that the disclosed methods for detecting and measuring glutamine analogues are adaptable as production (i.e., synthesis) methods for molecules related to indigoidine. Given the antibiotic properties of native indigoidine, it is likely that indigoidine-related molecules will have antimicrobial, antioxidant, or other useful activities. It is also likely that indigoidine-related molecules may comprise pigments with altered physical properties. e.g., different stability, intensity, or spectrum absorbance, as compared to native indigoidine.

EXAMPLES

The examples described herein are provided for the purpose of illustrating specific embodiments of the invention and are not intended to limit the invention in any way. Persons of ordinary skill can utilise the disclosures and teachings herein to produce other embodiments and variations without undue experimentation. All such embodiments and variations are considered to be part of this invention.

Example 1: Activation of BpsA Enzyme Post-Purification

Apo-BpsA was converted to holo-BpsA in vitro, post-purification, as follows. Purified BpsA and Sfp were obtained by standard Ni/NTA chromatography following their expression as His6-tagged recombinant polypeptides. The bpsA and sfp genes were cloned into and expressed from plasmid pET28a+ in $E.\ coli$ BL21 (DE3) cells, as described for BpsA and other PPTases by Owell et al (2011), with the modification that BpsA expression and purification was performed in an entD gene-deleted strain of $E.coli$ BL21(DE3). This was done to avoid any activation of BpsA by endogenous EntD PPTase prior to BpsA purification. The reagents were prepared as indicated in Table 1.

TABLE 1

| Reagent (indicated concentrations are as per final 100 µL reaction volume) |
| --- |
| 2 µM BpsA |
| 12.5 µM CoA |
| 0.1 µM Activating PPTase (Sfp from $B.\ subtilis$) |
| 5 mM $MgCl_2$ |
| 12.5 mM Tris pH 7.8 |
| $ddH_2O$ to 25 µL |

Reagents were added to a 15 ml tube. This was vortexed for two seconds and transferred to a 30° C. shaking incubator (200 rpm) for 20 minutes to enable 4'-PP attachment to occur. A negative control was set up in the same manner, omitting Sfp and adding 88.16 µL of $ddH_2O$ instead of 84.48 µL of $ddH_2O$.

Indigoidine synthesis reactions were performed in triplicate in a 96 well plate to assess whether activated BpsA was generated. For these reactions, 50 µL of 50 mM Tris-HCl, 10 mM $MgCl_2$ in $ddH_2O$ was added to each of six wells. Next, 25 µL of the reaction mix from Table 1 was added to each of the first three wells, and 25 µL of the negative control (unactivated BpsA) was added to the remaining 3 wells. Indigoidine synthesis was then initiated by addition of 5 mM ATP, 2 mM L-glutamine (indicated concentrations are as per final 100 µL reaction volume) from stocks prepared in 25 µL of $ddH_2O$ to each well. The 96 well plate was shaken at 1000 rpm and the $A_{590}$ values (absorbance at 590 nm) were recorded for each well every twenty seconds for 60 minutes. Triplicate data were averaged and graphed (FIG. 1).

FIG. 1 demonstrates that in vitro incubation with an activating PPTase (in this case, Sfp from $Bacillus\ subtilis$) is an effective means of pre-activating BpsA to enable indigoidine synthesis from L-glutamine. In the absence of an activating step, BpsA purified from a PPTase-deficient strain of $E.\ coli$ is unable to catalyse indigoidine synthesis. It was found that the PPTases PptT from $Mycobacterium\ tuberculosis$ and PcpS from $Pseudomonas\ aeruginosa$ are similarly able to activate BpsA following their over-expression and purification from $E.\ coli$ BL21(DE3) as His6-tagged recombinant polypeptides.

FIG. 1 further demonstrates the characteristic curve of indigoidine synthesis by BpsA in an aqueous environment. In the synthesis reaction, the $A_{590}$ of the solution initially increases, reaches a maximum, then diminishes to an intermediate minimum before gradually increasing once again. Examples 3 and 4 demonstrate how a standard curve for measurement of L-glutamine can be derived from this data.

Example 2: Activation of BpsA Enzyme Prior to Purification

It was further demonstrated that apo-BpsA is able to be converted to holo-BpsA prior to purification. The experiments were performed as follows. BpsA and the PPTase PcpS from *P. aeruginosa* were individually expressed as His6-tagged recombinant polypeptides from genes cloned into plasmid pET28a+ in separate 500 ml cultures of *E. coli* BL21(DE3) cells, as above. Following growth for 24 hours at 18° C., 200 rpm, the cultures were then individually pelleted and resuspended in Ni/NTA Bind buffer (pH 7.8, supplemented with 12.5% v/v glycerol). Each resuspended pellet was then lysed using a French press.

The cell lysates were then centrifuged at 31,000 g to separate the soluble and insoluble fractions. The BpsA and PcpS soluble fractions were mixed then supplemented with 100 μL of 10 mM CoA and incubated at 25° C. with shaking at 200 rpm for 2 hours. The mixed fraction was then centrifuged at 48,000 g for 20 minutes to remove the insoluble PcpS (which precipitates rapidly under the aforementioned incubation conditions). After this, standard Ni/NTA chromatography was used to recover BpsA as a His6-tagged recombinant polypeptide, as above. A 100 kDa cut off column was subsequently used to separate the purified BpsA from any residual PcpS, and triplicate reactions to test BpsA activity were prepared from a master mix in individual wells of a 96-well micro titre plate as indicated in Table 2.

TABLE 2

| Reagent (indicated concentrations are as per final 200 μL reaction volume) | Volume (μL) |
| --- | --- |
| 2 μM pre-activated BpsA | 4.9 |
| 50 mM Tris-HCl pH 7.8 | 10 |
| 20 mM MgCl$_2$ | 4 |
| ddH$_2$O | 71.1 |
| 5 mM ATP | 10 |
| Total | 100 |

Reactions for each replicate were initiated by addition of 100 μL of L-glutamine to a final concentration of 2 mM in ddH$_2$O. The 96 well plate was then shaken at 1000 rpm for 10 seconds and the A$_{590}$ values recorded every 20 seconds for one hour. The triplicate data sets were then averaged and graphed (FIG. 2).

From FIG. 2 it is evident that BpsA is able to be activated within cellular cytoplasm prior to purification. From this it can be concluded that cells co-expressing the bpsA gene as well as a gene that encodes a PPTase able to activate BpsA can be used as a source for high level production of pre-activated BpsA enzyme.

Example 3: Standard Curves Established for the BpsA Enzyme Assay Via Kinetic Measurements FIGS. 1 and 2 indicate that production of the blue pigment indigoidine by BpsA in aqueous solution yields a characteristic curve. It is observed that absorbance at 590 nm initially increases, reaches a maximum, then diminishes to an intermediate minimum before slowly increasing once again. The reasons for this characteristic reaction curve are still under investigation, but it may reflect the poor solubility of indigoidine in H$_2$O.

Experiments were then performed to determine whether the BpsA-catalysed conversion of L-glutamine into indigoidine can be used to estimate the starting concentration of L-glutamine present in a solution. The experiments employed kinetic measurements derived from the initial peak of indigoidine production.

For this investigation, the following L-glutamine concentration standards were each prepared in ddH$_2$O at a final volume of 100 μL in individual wells of a 96-well microtitre plate: 1000 μM, 800 μM, 600 μM, 400 μM, 200 μM, and 0 μM. Next, 10 μL of each L-glutamine standard was pipetted in triplicate into separate wells of a 96 plate well. Following this, 40 μL of ddH$_2$O was added to each well. To initiate indigoidine synthesis, 50 μL aliquots of a master mix with final reagent concentrations as indicated in Table 3 were added to each well.

TABLE 3

| Reagent (indicated concentrations are as per final 100 μL reaction volume) |
| --- |
| 50 mM Tris-HCL pH 7.8 |
| 20 mM MgCl$_2$ |
| 5 mM ATP |
| 2 μM holo-BpsA (pre-activated as per Example 2) |
| ddH$_2$O to a final volume of 50 μL |
| Total volume 50 μL per well |

The plate was then immediately shaken at 1000 rpm for 10 seconds, after which it was incubated at room temperature and the A$_{590}$ values were recorded every 20 seconds for one hour. The triplicate data sets were then averaged and graphed (FIG. 3A).

Figure 3A:
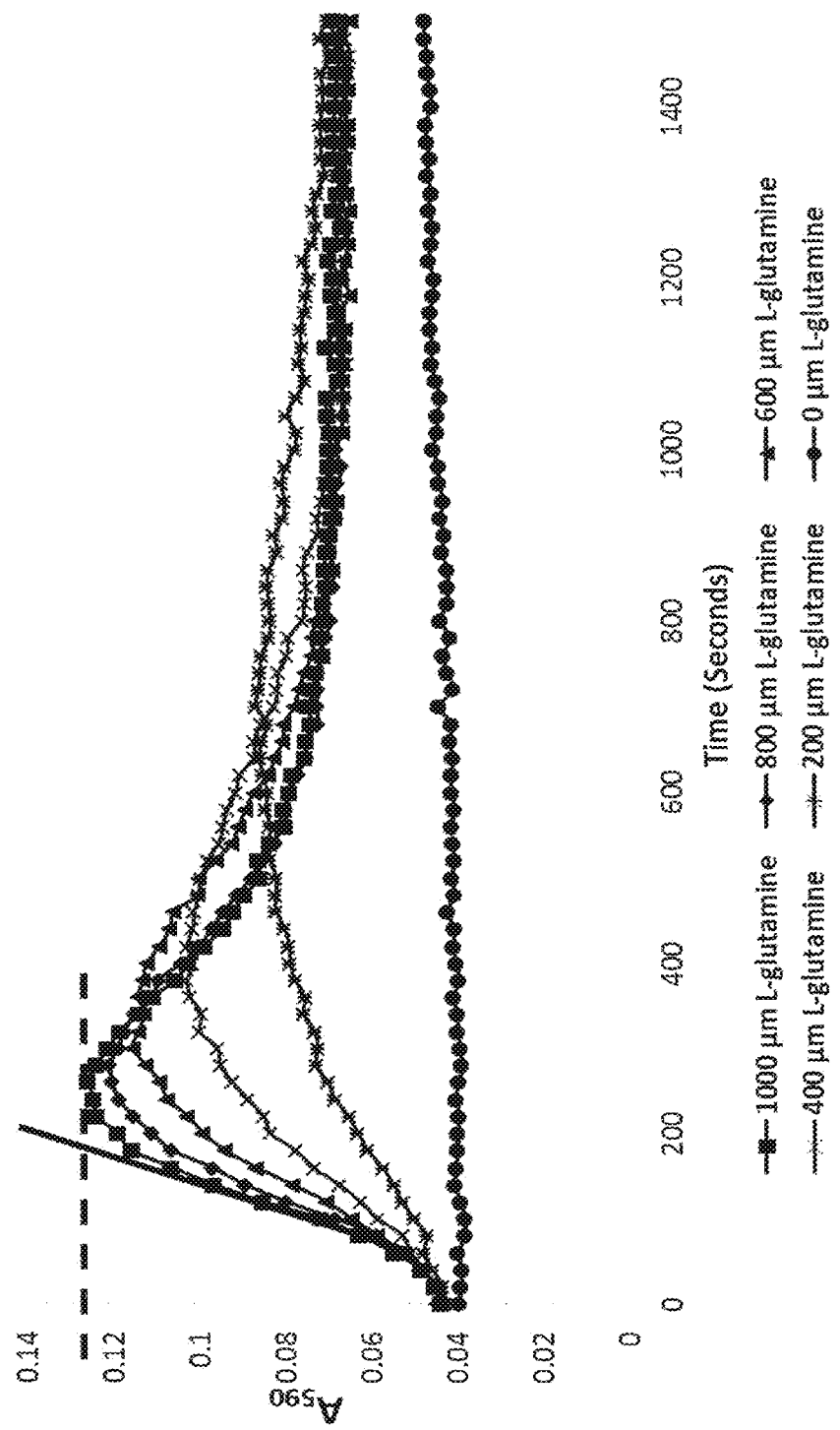

It was found that both maximal velocity of indigoidine production (i.e., the steepest slope of the initial indigoidine production curve; indicated by a solid line for the 1000 μM L-glutamine standard in FIG. 3A) and the maximum absorbance attained in the initial indigoidine production curve (indicated by a dashed line for the 1000 μM L-glutamine standard in FIG. 3A) can be employed to generate a linear standard plot across a range of concentrations up to 600 μM L-Glutamine in water (FIG. 3B, FIG. 3C). Beyond 600 μM L-glutamine, the reaction starts to saturate and the standard curve becomes less linear.

It was concluded that it is possible to generate standard curves using kinetic measurements of BpsA, based on either the maximal velocity of indigoidine production or the maximum absorbance attained in the initial indigoidine production curve. These methods are less sensitive and have less of a dynamic range than the preferred (end-point) assay format described in Example 4. Nonetheless, the kinetic assays may be used for rapid assessment of L-glutamine concentrations. Additionally, such assays may be used where the test sample reacts with DMSO in a manner that confounds the A$_{590}$ measurements.

Example 4: Standard Curve Established for the BpsA Assay Via End-Point Quantification of Re-Solubilised Indigoidine For improved accuracy, reproducibility, and robustness, it is generally preferable to use an end-point assay over a kinetic assay. An end-point assay for BpsA was designed and carried out as follows. In these experiments, 40 μL indigoidine-producing reactions were run until all glutamine present was consumed, and then all the indigoidine was solubilised by adding 190 μL of the organosulfur solvent dimethyl sulfoxide (DMSO). It was found that this approach generally yields a standard curve with a better straight line fit than the kinetic assay approach detailed in Example 3.

For this assay, the following L-glutamine concentration standards were each prepared in ddH$_2$O at a final volume of 100 μL in individual wells of a 96-well microtitre plate:

1000 µM, 800 µM, 600 µM, 400 µM, 200 µM, and 0 µM. A master mix with final reagent concentrations as indicated in Table 4 was prepared and dispensed into 18 fresh wells of a 96 well plate at a volume of 30 µL per well.

TABLE 4

Reagent (indicated concentrations are as per final 40 µL reaction volume)

50 mM Tris-HCl pH 7.8
20 mM MgCl$_2$
5 mM ATP
2 µM holo-BpsA (pre-activated as per Example 2)
ddH$_2$O to a total volume of 30 µL per well
Total volume 30 µL per well Indigoidine synthesis reactions were initiated by addition of 10 µL of each L-glutamine concentration standard in triplicate. This was done by the addition of 10 µL of 1000 µM L-glutamine to three of the 18 mastermix containing wells; addition of 800 µM L-glutamine to three wells; and so on down to addition of 0 µM L-glutamine to the final three wells. The 96 plate was then mixed at 1000 rpm for 10 seconds and incubated at room temperature for 45 minutes to enable complete reaction of all L-glutamine present in each well. After this, 190 µL of DMSO heated to 50° C. was added to each well to solubilise the indigoidine. The 96 well plate was then incubated at room temperature with shaking at 2500 rpm for 10 minutes. The A$_{590}$ value for each well was determined spectrophotometrically and then the three values obtained for each standard were averaged and the mean data graphed. This yielded a standard curve with an excellent straight line fit (FIG. 4).

It was concluded that the robust nature of this end-point assay and the excellent fit of the standard curve makes this an ideal format for measuring the L-glutamine in any sample that is amenable to a 30 µL reaction volume and tolerant of addition of DMSO without cross-reaction of other constituents present. Further experiments showed this assay to be suitable for most complex biological media (see Example 6, further below).

Example 5: Analysis of BpsA Functionality in the Presence of the Organosulfur Solvent DMSO It was next tested whether the BpsA enzyme would function in the presence of sufficient concentrations of DMSO to maintain solubility of indigoidine throughout the reaction. From these experiments, it was discovered that BpsA retains partial functionality at up to 35% DMSO, and that concentrations of DMSO above 30% are sufficient to maintain indigoidine solubility; however, the partial functionality of BpsA at concentrations above 30% DMSO is insufficient to enable complete conversion of all L-glutamine present.

In these experiments, samples of 500 µM L-glutamine were prepared in ddH$_2$O amended with DMSO to a final DMSO concentration (v/v) of either 0%, 10%, 20%, 30% or 35%. A master mix with final reagent concentrations as indicated in Table 5 was prepared and dispensed into 18 wells of a fresh 96 well plate at a volume of 20 µL per well.

TABLE 5

Reagent (indicated concentrations are as per final 50 µL reaction volume)

50 mM Tris-HCl pH 7.8
20 mM MgCl$_2$

TABLE 5-continued

Reagent (indicated concentrations are as per final 50 µL reaction volume)

5 mM ATP
2 µM holo-BpsA (pre-activated as per Example 2)
ddH$_2$O to a total volume of 20 µL per well
Total volume 20 µL per well Indigoidine synthesis reactions were initiated by addition of 30 µL of each L-glutamine containing DMSO concentration standard in triplicate. This was done by addition of 30 µL of 500 µM L-glutamine in 35% DMSO to three of the 18 mastermix containing wells; addition of 500 µM L-glutamine in 30% DMSO to three wells; and so on down to addition of 500 µM L-glutamine in DMSO-free ddH$_2$O to three wells. Three negative control wells (containing mastermix, but with ddH$_2$O added in place of glutamine) were also prepared. The 96 well plate was then immediately mixed at 1000 rpm and the A$_{590}$ values were then recorded using a plate reader for every 20 seconds for 60 minutes. The three values obtained for each standard were averaged and the mean data graphed (FIG. 5A).

Figure 5A:
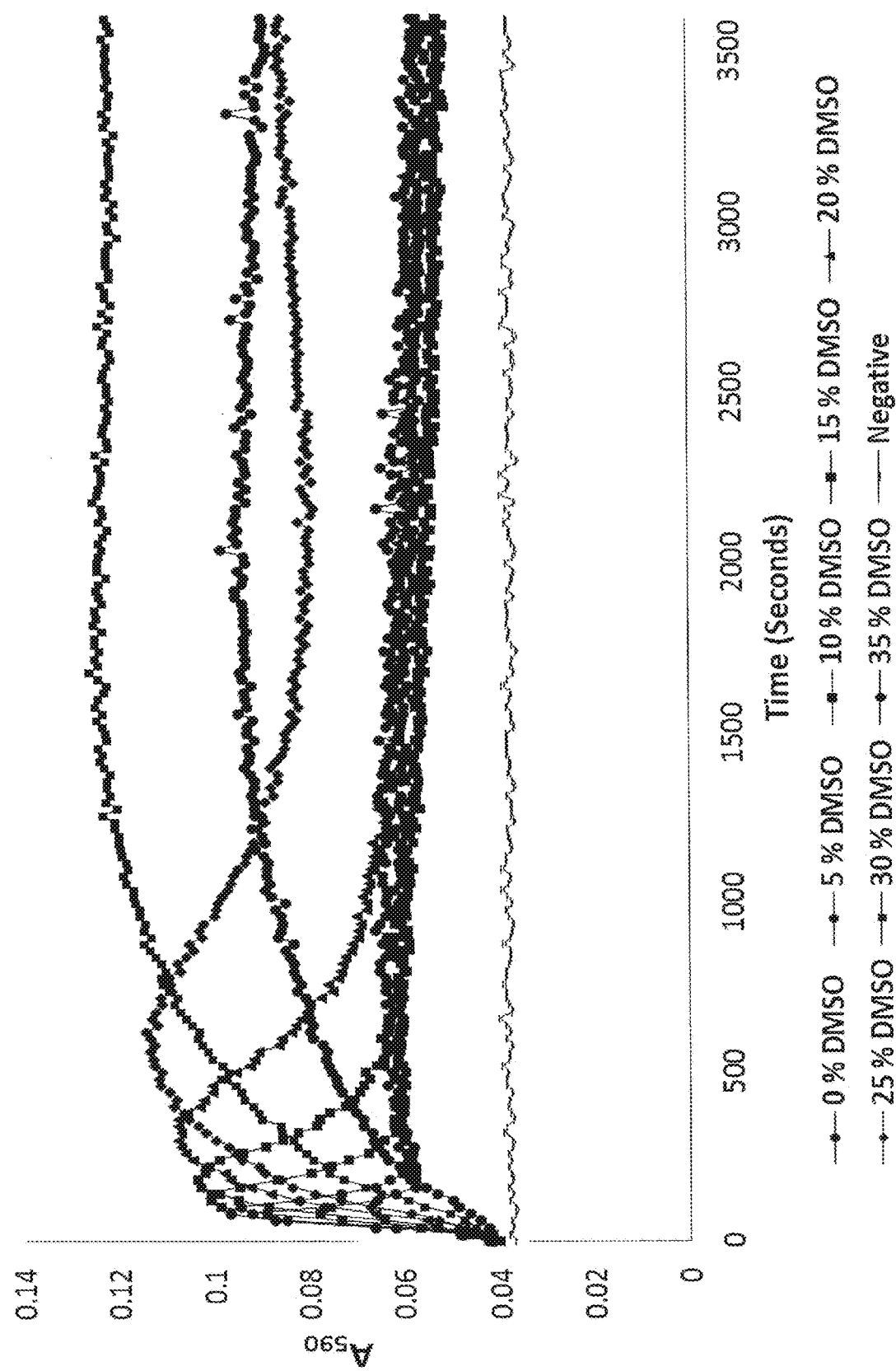

It initially appeared that based on the reaction profile in FIG. 5A, BpsA was fully active at 30% DMSO, a concentration that was sufficient to maintain solubility of indigoidine. However, at 35% DMSO indigoidine synthesis levelled off at a lower maximum value than was observed at 30% DMSO, suggesting that enzyme activity had been impaired and not all L-glutamine had been converted to indigoidine. This in turn suggested that the reaction at 30% DMSO may also not have achieved complete L-glutamine conversion.

To test whether full L-glutamine conversion had been achieved in the presence of DMSO, 180 µL of DMSO heated to 50° C. was then added to each well to completely solubilise the indigoidine. The 96 well plate was then incubated at room temperature with shaking at 2500 rpm for 10 minutes. Following this, a single A$_{590}$ reading was taken and the average of the triplicate values were graphed (FIG. 5B).

The data presented in FIG. 5B indicates that BpsA activity was impaired at all concentrations of DMSO, with the degree of impairment proportional to the concentration of DMSO present. Thus, it was concluded that it is not generally appropriate to add DMSO to the primary reaction mixture. Nonetheless, these data provide evidence that BpsA may be able to accurately measure L-glutamine in the presence of organic co-solvents provided a suitable standard curve is established in the presence of the same co-solvents.

Example 6: Measurement of L-Glutamine in Complex Biological Media

It was next tested whether the BpsA end-point assay can be used to monitor L-glutamine concentrations in complex biological media including blood serum, urine, lysogeny broth (LB; bacterial cell culture medium), and Dulbecco's modified Eagle's medium (DMEM; eukaryotic cell culture medium).

For these experiments, standard samples (10 µL per well) were prepared in triplicate in ddH$_2$O as per Example 4 at the following concentrations: 1000 µM, 800 µM, 600 µM, 400 µM, 200 µM, and 0 µM. Alongside these were aliquoted paired triplicate samples (10 µL per well) of the following media: adult bovine serum (purchased from Sigma-Aldrich), human urine, LB, DMEM, and ddH$_2$O. For each medium, one of the two paired triplicate sets was spiked (amended)

with 300 μM L-glutamine, while the other was left unspiked. Indigoidine synthesis was initiated by addition of 30 μL reaction mix (as described in Table 4) to each sample-containing well. The 96 well plate was then mixed at 1000 rpm for 10 seconds and incubated at room temperature for one hour, after which 180 μL of DMSO heated to 50° C. was added to each well. The plate was then shaken at 2500 rpm for 10 minutes to fully solubilise the indigoidine.

It was observed that the serum containing wells went immediately cloudy upon addition of DMSO, preventing meaningful $A_{590}$ readings from being obtained for those samples. In all other cases, a single $A_{590}$ reading for each well was recorded. For each sample, triplicate $A_{590}$ values were averaged and this value was used to quantify glutamine levels based on the standard curve generated from the standard samples. With the exception of the ddH$_2$O, it was unknown what the starting concentration of L-glutamine was in each medium being tested. However, the comparison of measured L-glutamine levels in spiked versus unspiked samples for each medium enabled assessment of the accuracy of the BpsA end-point assay in measuring L-glutamine concentrations in that medium. These data are summarised in Table 6.

TABLE 6

| Sample | Spiked sample measurement (μM L-glutamine +/− 1 std dev) | Unspiked sample measurement (μM L-glutamine +/− 1 std dev) | Spiked − unspiked (μM L-glutamine +/− 1 std dev) |
|---|---|---|---|
| LB | 377.9 ± 14.1 | 49.6 ± 5.3 | 328.1 ± 15.2 |
| DMEM | 427.4 ± 4.6 | 20.3 ± 2.7 | 407.0 ± 5.4 |
| ddH$_2$O | 319.0 ± 5.4 | 0 | 319.0 ± 5.4 |
| Urine | 295.8 ± 7.1 | 71.4 ± 23.6 | 224.4 ± 24.9 |

These data indicate that the BpsA endpoint assay is relatively accurate in measuring L-glutamine in LB and ddH$_2$O. When comparing against a standard curve prepared in ddH$_2$0. the assay slightly underestimates the levels of L-glutamine present in urine and overestimates the levels of L-glutamine present in DMEM. In view of this, it is proposed that assay optimisation can be achieved for each sample type. In particular, for DMEM a standard curve can be prepared in glutamine-depleted DMEM rather than ddH20. For urine, the pH can be neutralised prior to sample testing. However, the results appear to indicate that serum is not compatible with the use of DMSO in the end-point assay format.

Example 7: Detection of L-Glutamine in Blood Plasma

As it was not possible to measure L-glutamine in blood (serum) using the BpsA end-point assay, it was investigated whether a kinetic assay can be used for measuring blood glutamine levels.

For these experiments, a blood sample was taken from a healthy male and centrifuged to isolate the plasma. A triplicate 2-fold serial dilution series was established using ddH$_2$O (from 100% down to 0.19% plasma). An identical serial dilution of blood plasma spiked with 1.3 μL of 100 mM L-glutamine (from 100% down to 0.19% plasma) was also established in the 96 well plate. A negative control containing only ddH$_2$O was also established. 25 μL of reaction buffer (Table 7) was then added to each well.

TABLE 7

Reagent (indicated concentrations are as per final 100 μL reaction volume)

43 mM Tris-Cl pH 7.8
10 mM ATP
8.8 mM MgCl$_2$
ddH$_2$O to 25 μL
Total 25 μL per well Indigoidine synthesis reactions were then initiated by addition of 25 μL of buffered pre-activated BpsA to each well (pre-activated as described in Example 1: final BpsA concentration of 1.66 μM). The 96 well plate was mixed by shaking at 1000 rpm for 10 seconds and immediately read at 590 nm in an EnSpire® plate reader every 30 seconds for 30 minutes. Each concentration of blood plasma was analysed in triplicate and each concentration of blood plasma spiked with L-glutamine was analysed in duplicate. The maximum $A_{590}$ values were generated by averaging the triplicate and duplicate repeats, respectively.

Figure 6:
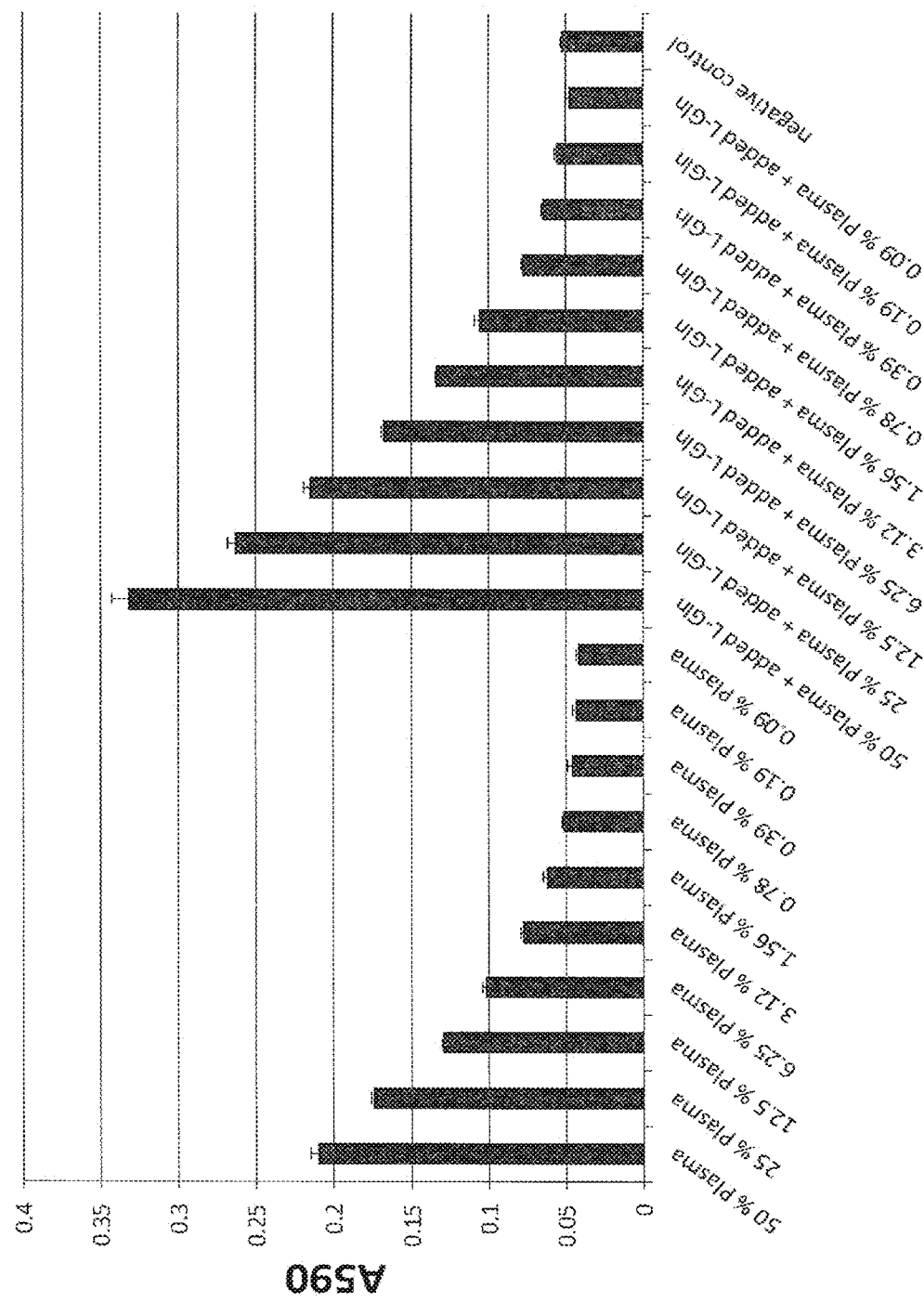
FIG. 6: The BpsA kinetic assay (maximum absorbance method) for measuring L-glutamine levels in blood plasma. Comparison of maximum $A_{590}$ values of serial diluted plasma and plasma spiked with L-glutamine. Data was generated from triplicate repeats, and error bars represent the standard error of each data set.

The mean maximum $A_{590}$ value for each plasma dilution is shown in FIG. 6. The spiked plasma data indicates that that BpsA kinetic assays can be used to accurately estimate the concentration of L-glutamine in blood down to low micromolar levels.

Example 8: Measurement of L-Glutamine in Bacterial Cultures

It was further demonstrated that the BpsA enzyme assay can be used to monitor L-glutamine concentrations in bacterial cultures grown in a medium such as lysogeny broth (LB). It was found that the reaction still proceeds under these conditions and a near-linear correspondence between the absorbance and the amount of L-glutamine can be seen.

In these experiments, a two-fold serial dilution of L-glutamine was set up in triplicate in 20 μL per well in a 96 well plate, across a range of 0.5 to 8.0 mM. This yielded a final concentration range of 0.1 to 1.6 mM in the ultimate 100 μL reaction volumes. Each well was then mixed with 30 μL of an overnight culture of E. coli grown in LB ($A_{600}$ (absorbance of undiluted culture at 600 nm)=2.7), and 25 μL of reaction buffer, which yielded final reagent concentrations as shown in Table 8.

TABLE 8

Reagent (indicated concentrations are as per final 100 μL reaction volume)

5 mM ATP
8.8 mM MgCl$_2$
5 mM Ascorbic Acid
100 mM Tris-Cl pH 8.0
ddH$_2$O to a total volume of 25 μL per well
Total volume 25 μL To initiate the indigoidine synthesis reactions, 25 μL of pre-activated BpsA (prepared as shown in Table 9) was added. The plate was mixed at 1000 rpm for 5 seconds and absorbance was read at 590 nm every 20 seconds for 90 repeats in a plate reader.

TABLE 9

| Reagents (final concentration) |
| --- |
| 3.25 µM BpsA |
| 100 µM CoA |
| 1.6 µM PptT |
| 10 mM MgCl$_2$ |
| 50 mM Tris pH 7.8 |
| ddH$_2$O to a total volume of 25 µL per well |
| Total volume 25 µL |

The experiments used a final cell density ($A_{600}$) of 0.81. As the $A_{600}$ reading can interfere with the $A_{590}$ readings of indigoidine, negative controls containing no L-glutamine were used. The final $A_{590}$ values were derived by subtracting the $A_{590}$ of the negative control from the maximum $A_{590}$ value achieved in each indigoidine synthesis reaction.

Figure 7:
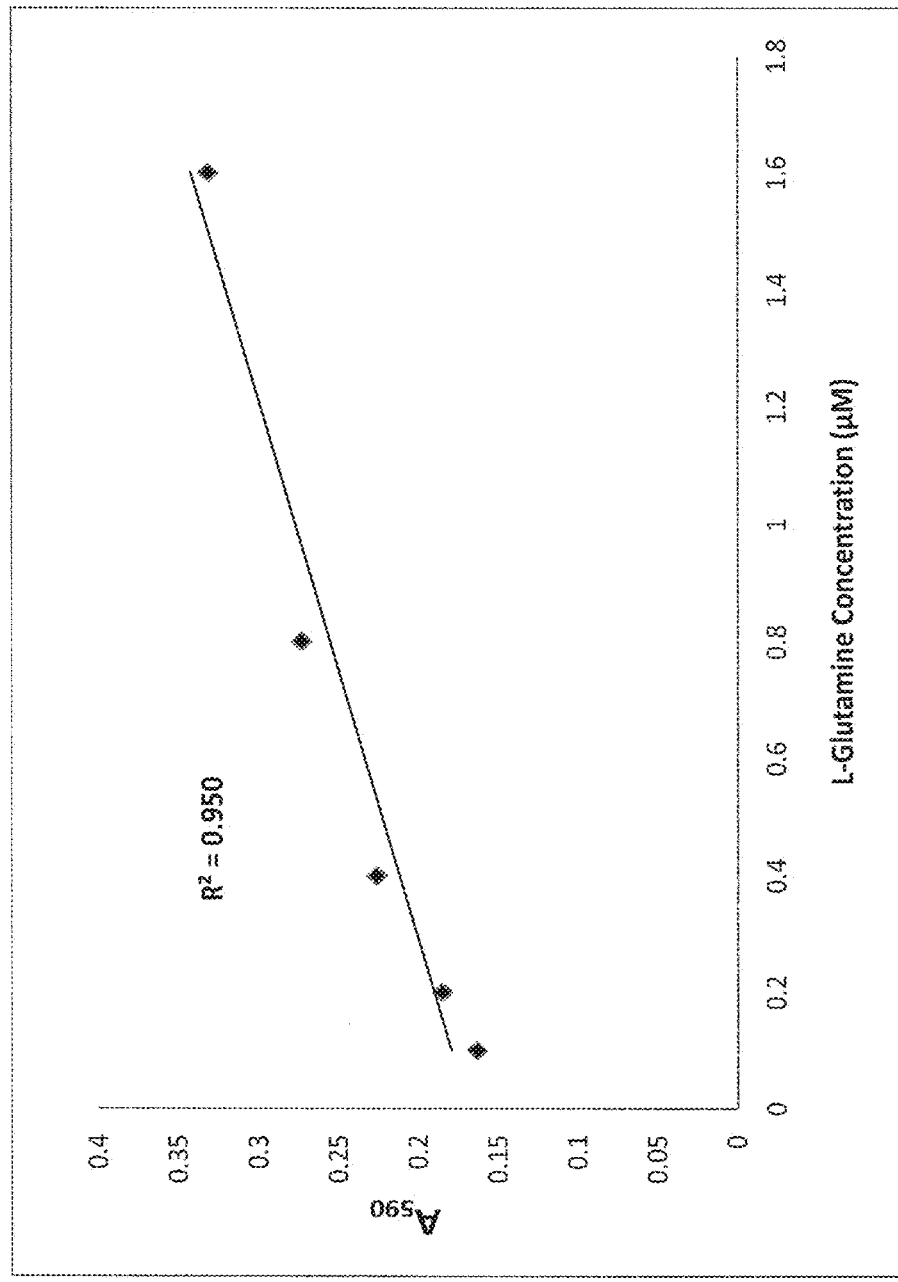
FIG. 7: Standard curve for the BpsA kinetic assay (maximum absorbance method) using a serial dilution of 0.1 to 1.6 mM L-glutamine in a diluted overnight culture of E. coli.

Using this methodology, serial dilutions of L-glutamine were tested in LB cultures of growing E. coli cells. FIG. 7 depicts the maximum absorbance values achieved across a series of standard L-glutamine concentrations prepared in this manner. For unamended LB media, a linear relationship was observed up to the maximum tested L-glutamine concentration of 400 µM. A linear relationship was observed up to the second highest tested L-glutamine concentration of 800 µM. Consistent with the previous results using the maximum absorbance kinetic assay (FIG. 3C), linearity was not observed above this concentration. Nevertheless, the ability to measure glutamine concentrations in the presence of actively growing cells suggests that the BpsA assay can be used for screening variants of glutamine-producing bacterial strains. In turn, such screening can be used to identify the variants that are the most active in glutamine production.

Example 9: Stability of BpsA Over Time

An important property of any enzyme to be used in a kit is retention of activity after short or preferably long term storage, at refrigerated or more preferably room temperature conditions.

To monitor stability of Bps A over time after storage at these conditions, two BpsA samples were stored, one at 25° C. and one at 4° C. The two samples were then compared to recently purified BpsA. The BpsA stored at 4° C. retained 96% activity and the BpsA stored at 25° C. retained 15% activity after 24 weeks compared to the recently purified BpsA. These data suggest that BpsA is highly stable long term at 4° C. and is robust enough to tolerate 25° C. for moderate periods of time.

Example 10: Identification of Glutamine Analogues and Generation of Indigoidine-Related Molecules Additional experiments were performed to identify glutamine analogues and generate indigoidine-related molecules.

Figure 8A:
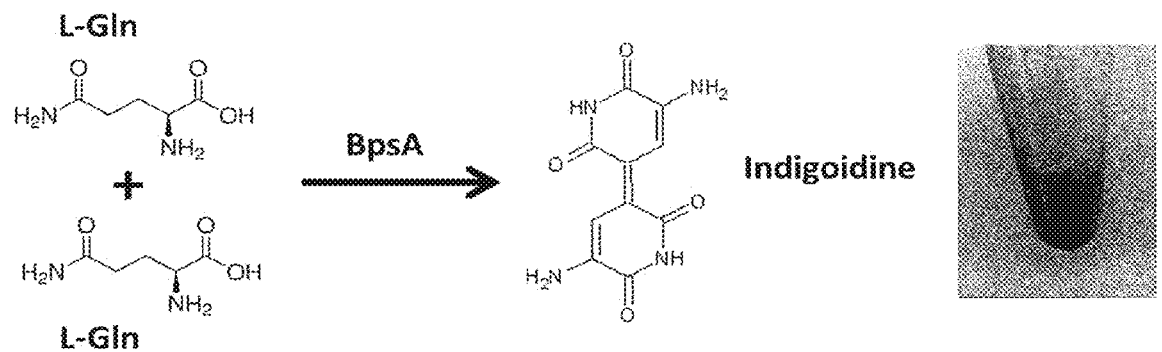
FIG. 8A through FIG. 8E: BpsA-mediated synthesis of indigoidine-related pigments from different L-glutamine analogues.

From the structures of L-glutamine and indigoidine (FIG. 8A), it can be inferred that the two heterocyclic rings of indigoidine are formed via intramolecular condensation reactions between the carboxyl group attached to the a-carbon and the sidechain amino group attached to the δ-carbon of each L-glutamine substrate. In contrast, the amino groups originally attached to the α-carbon of each L-glutamine substrate are displayed as an unreacted substituent on each heterocyclic ring. Based on this, it was hypothesised that BpsA could cyclise derivatives of L-glutamine that include other molecules attached to the amino group of each a-carbon (e.g., peptides terminating in L-glutamine).

For these experiments, BpsA activation was carried out as noted in Example 1. Pre-activated BpsA was incubated at 25° C. for 72 hours in reaction buffer amended with 4 mM of either L-glutamine, L-glycine-L-glutamine (glycyl glutamine), L-alanine-L-glutamine (alanyl glutamine), N-trifluoracetyl-L-glutamine, or no substrate as a control. Pre-activated and buffered BpsA at a final concentration of 1.66 µM was added to a reaction buffer containing 4 mM of each L-glutamine derivative in a final reaction volume of 1000 µL. This was then incubated al 25° C. for 72 hours. Each reaction tube was centrifuged and the supernatant removed. The indigoidine derivatives were then resuspended in 100 µL of 99.9% DMSO to solubilise the precipitated pigment.

Figure 8B:
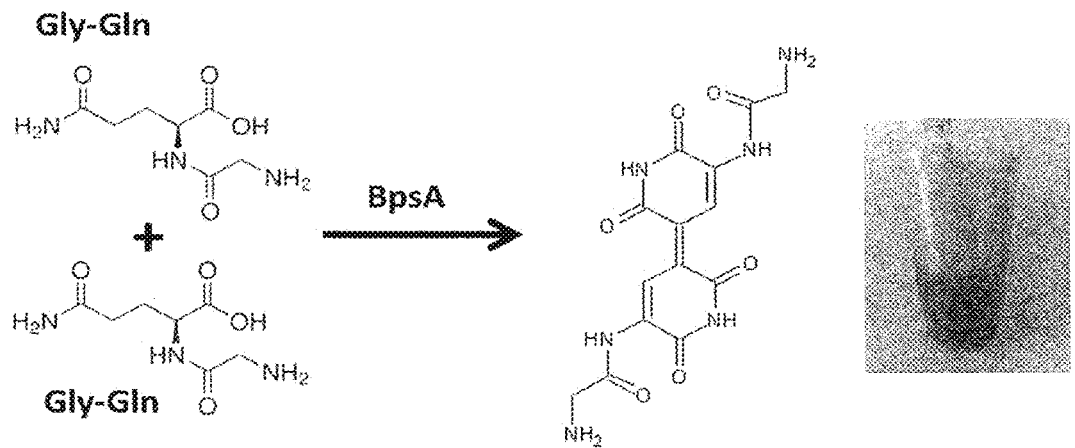
Figure 8C:
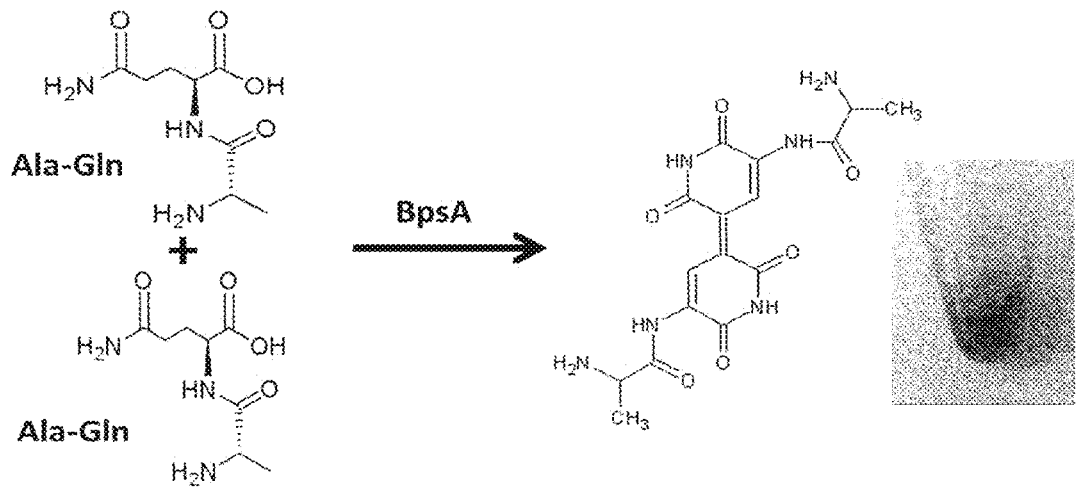
Figure 8D:
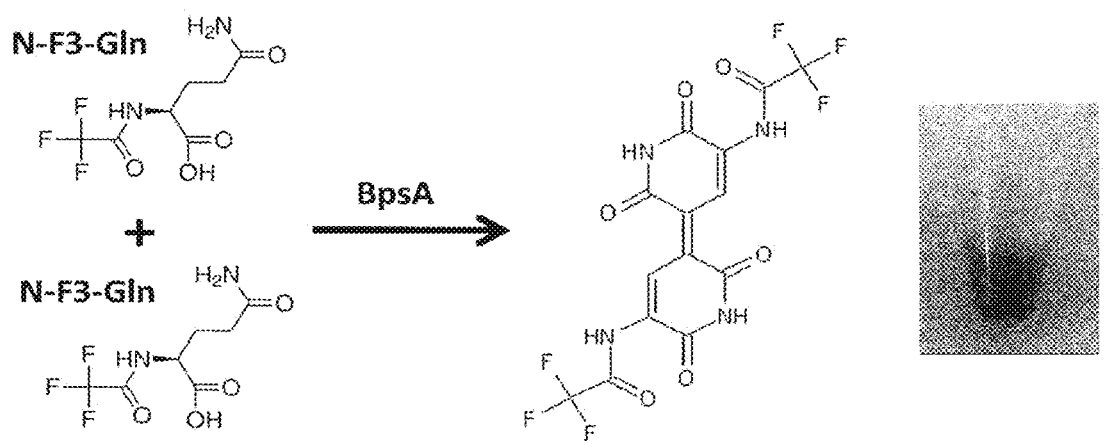
Figure 8E:
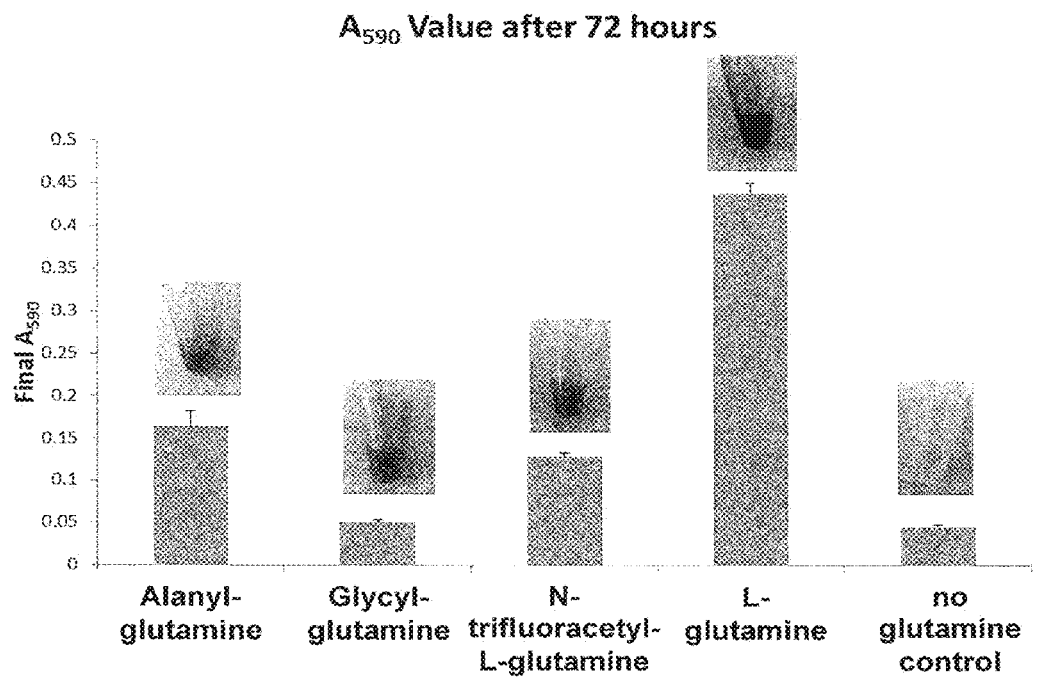

The structures of each substrate and the predicted structure of the cyclised indigoidine-like product potentially produced in each reaction are depicted in FIGS. 8B-4D. In each case except the no substrate control, blue pigment formation was observed, suggesting that an indigoidine like product had indeed been formed. The relative absorbance levels of each reaction at the end of the 72 hour incubation period are illustrated in FIG. 8E.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the scope and/or essential characteristics of the present invention.

Accordingly, one of ordinary skill in the art will readily appreciate from the disclosure that later modifications, substitutions, and/or variations performing substantially the same function or achieving substantially the same result as embodiments described herein may be utilised according to such related embodiments of the present invention. Thus, the invention is intended to encompass, within its scope, the modifications, substitutions, and variations to processes, manufactures, compositions of matter, compounds, means, methods. and/or steps disclosed herein.

REFERENCES

Agostini F., Biolo G. (2010) Effect of physical activity on glutamine metabolism. Current Opinion in Clinical Nutrition and Metabolic Care 13: 58-64.

Altschul et al., (1997) Nuc. Acid Res, 25: 3389-3402.

Barekzi N., Joshi S., Irwin S., et al. (2004) Genetic characterization of pcpS, encoding the multifunctional phosphopantetheinyl transferase of Pseudomonas aeruginosa. Microbiology, 150: 795-803.

Bowie et al. (1990) Science, 247: 1306.

Castell L. M., Newsholme E. A. (1997) Nutrition, 13(7-8): 738-42.

Challis G. L., Naismith J. H. (2004) Structural aspects of non-ribosomal peptide biosynthesis. Curr Opin Struct Biol., 14(6): 748-756.

Chalut C., Botella L., de Sousa-D'Auria C., Houssin C., Guilhot C. (2006) The nonredundant roles of two 4'-phosphopantetheinyl transferases in vital processes of Mycobacteria. Proc Natl Acad Sci USA, 30;103(22): 8511-6.

Jianmin Chen and Karl Herrup (2012) PLoS One, 7(3): e33177.

Darmaun, D., Manary, M. J., & Matthews, D. E. (1985) A method for measuring both glutamine and glutamate levels and stable isotopic enrichments. Analytical Biochemistry, 147(1): 92-102.

Duchaud, E., Rusniok, C., Frangeul, L., Buchrieser, C., Givaudan, A., Taourit, S., Bocs, S., Boursaux-Eude, C., Chandler, M., Charles, J. F., Dassa, E., Derose, R, Derzelle, S., Freyssinet, G., Gaudriault, S., Medigue, C., Lanois, A., Powell, K., Siguier, P., Vincent, R., Wingate, V., Zouine, M., Glaser. P., Boemare. N., Danchin, A., and Kunst, F. (2003) Nat. Biotechnol., 21: 1307-1313.

Duckworth et al., (2010) Anal. Biochem., 403:13-19.

Robert Finking and Mohamed A. Marahiel (2004) Biosynthesis of nonribosomal peptides, Annu. Rev. Microbiol., 58: 453-488.

Foley et al. (2009) FEBS J., 276:7134-714.5.

Gehring A. M., Lambalot R. H., Vogel K. W., Drucckhamcr D. G., Walsh C. T. (1997) Chem. Biol., 4: 17-24.

Gronwald v V., Klein M. S., Zeltner R., Schulze B. D., Reinhold S. W., Deutschmann M., Immervoll A. K., Böger C. A., Banas B., Eckardt K. U., Oefner P. J. (2011) Kidney Int. 79(11): 1244-53.

Guzman et al., (1995) J. Bacteriol., 177(14): 4121-4130.

Hitoshi Takahash, Takanori Kumagai, Kyoko Kitani, Miwako Mori. Yasuyuki Matoba, and Masanori Sugiyama (2007) Cloning and characterization of a *Streptomyces* single module type non-ribosomal peptide synthetase catalyzing a blue pigment synthesis. J. Biol. Chem., 282: 9073-9081.

Hanahan, D. (1983) Studies on transformation of *Escherichia coli* with plasmids. Journal of Molecular Biology, 166(4): 557-580.

Hermann, Thomas (2003) Industrial production of ammo acids by Coryneform bacteria. Journal of Biotechnology, 104 (1-3): 155-172.

Huang, X. (1994) On global sequence alignment. Computer Applications in the Biosciences, 10: 227-235.

Ikeda A., Nishiumi S., Shinohara M., Yoshie T., Hatano N., Okuno T., Bamba T., Fukusaki E., Takenawa T., Azuma T., Yoshida M. (2012) Serum metabolomics as a novel diagnostic approach for gastrointestinal cancer. Biomedical Chromatography 26: 548-558.

Jakoby, Marc, Reinhard Kramer, and Andreas Burkovski (1999) Nitrogen regulation in *Corynebacterium glutamicum*: isolation of genes involved and biochemical characterization of corresponding proteins. FEMS Microbiology Letters, 173(2): 303-310.

Jakoby, Marc, Martin Tesch, Hemlann Sahm, Reinhard Kramer, and Andreas Burkovski. (1997) Isolation of the *Corynebacterium glutamicum* glnA gene encoding glutamine synthetase I. FEMS Microbiology Letters, 154(1): 81-88.

Anil K. Joshi, Lei Zhan, Vangipuram S. Rangan, and Stuart Smith (2003) Cloning, expression, and characterization of a human 4'-phosphopantetheinyl transferase with broad substrate specificity. The Journal of Biological Chemistry, 278: 33142-33149.

Karoum F., Chuang L. W., Mosnaim A. D., Staub R. A., Wyatt R. J. (1983) J Chromatogr Sci., 21(12): 546-50.

Konz, D., and Marahiel, M. A. (1999) Chem. Biol., 6: 39-48.

Kuhn, R., Stan, M. P., Kuhn, D. A., Bauer, H., and Knackmuss, H. J. (1965) Indigoidine and other bacterial pigments related to 3,3'-bipyridyl. Archives of Microbiology 51(1): 71-84.

Kusumoto, Isao (2001) Industrial production of L-glutamine. The Journal of Nutrition, 131(9): 2552S-2555S.

Li, Jinshan, Cuiqing Ma, Yanhe Ma, Yan Li, Wei Zhou, and Ping Xu. (2007) Medium optimization by combination of response surface methodology and desirability function: an application in glutamine production. Applied Microbiology and Biotechnology, 74(3): 563-571.

Liu, Qian, Jiao Zhang, Xiao-Xing Wei, Shao-Ping Ouyang, Qiong Wu, and Guo-Qiang Chen (2008) Microbial production of L-glutamate and L-glutamine by recombinant *Corynebacterium glutamicum* harboring *Vitreoscilla* hemoglobin gene vgb. Applied Microbiology and Biotechnology, 77(6): 1297-1304.

McKenzie D. C. (1999d) Markers of excessive exercise. Canadian Journal of Applied Physiology 24: 66-73.

Marahiel et al. (1997) Chemical Reviews, 97: 2651-2673.

Marahiel, M. A. and L. O. Essen (2009) Nonribosomal peptide synthetases: Mechanistic and structural aspects of essential domains. Methods in Enzymology, 458:337-351.

Meier, J. L. and M. D. Burkart (2009) The chemical biology of modular biosynthetic enzymes. Chemical Society Reviews, 38(7): 2012-2045.

Mootz H. D., Finking R., Marahiel M. A. (2001) J. Biol. Chem., 276: 37289-37298.

Morlion, B. J.; Stehle, P.; Wachtler, P.; Siedhoff, H. P.; Koller, M.; Konig, W., Furst, P., Puchstein, C. (1998) Annals of Surgery, 227(2): 302-308.

Mortimer, P. S., Gladys. C., and Hans-Joachim, K. (1966) Appl. Microbiol., 14: 870-872.

Müller M, Auslander S, Auslander D, Kemmer C, Fussenegger M. (2012) A novel reporter system for bacterial and mammalian cells based on the non-ribosomal peptide indigoidine. Metabolic Engineering, 14(4): 325-335.

Nabe, Koichi, Shigeki Yamada, and Ichiro Chibata (1981) Mechanism of L-glutamine production by an L-glutamine-producing mutant of Flavobacterium rigense. Applied and Environmental Microbiology, 42(4): 605-610.

Needleman, S. B. and Wunsch, C. D. (1970) J. Mol. Biol., 48: 443-453.

Newsholme, P. (2001) Why is L-glutamine metabolism important to cells of the immune system in health, postinjury, surgery or infection? The Journal of Nutrition, 131(9):2515S-25225.

Owen J. G., J. N. Copp and D. F. Ackerley (2011) Rapid and flexible biochemical assays for evaluating 4'-phosphopantetheinyl transferase activity. Biochemical Journal, 436: 709-717.

Owen, J. G., Robins, K. J., Parnchin, N. S., & Ackerley, D. F. (2012) A functional screen for recovery of 4'-phosphopantetheinyl transferase and associated natural product biosynthesis genes from metagenome libraries. Environmental Microbiology, 14(5): 1198-1209.

Petibois C., Cazorla G., Poortmans J. R., Déléris G. (2002) Biochemical aspects of overtraining in endurance sports: a review. Sports Medicine 32: 867-878.

Quadri L. E., Weinreb P. H., Lei M., Nakano M. M., Zuber P., Walsh C. T. (1998) Characterization of Sfp, a *Bacillus subtilis* phosphopantetheinyl transferase for peptidyl carrier protein domains in peptide synthetases. Biochemistry. 37(6): 1585-95.

Rice, P. et al. (2000) EMBOSS: The European Molecular Biology Open Software Suite, Trends in Genetics, 16(6): 276-277.

Rehm, Nadine, and Andreas Burkovski (2011) Engineering of nitrogen metabolism and its regulation in *Corynebacterium glutamicum*: influence on amino acid pools and production. Applied Microbiology and Biotechnology, 89(2): 239-248.

Reverchon, S., Rouanet, C., Expert, D., and Nasser, W. (2002) J. Bacteriol., 184:654-665.

Sambrook, J. and D. W. Russell (2003) Molecular Cloning: A Laboratory Manual, Cold Spring Harbour Laboratory Press.

Sambrook, J. and D. W. Russell (2006) Transformation of *E. coli* by Electroporation. Cold Spring Harbor Protocols.

Sánchez C., Du L., Edwards D. J., Toney M. D., Shen B. (2001) Cloning and characterization of a phosphopantetheinyl transferase from *Streptomyces verticillus* ATCC15003, the producer of the hybrid peptide-polyketide antitumor drug bleomycin. Chem Biol., 8(7): 725-38.

Shockcor J. P., Unger S. E., Wilson I. D., Foxall P. J, Nicholson J. K., Lindon J. C. (1996) Anal Chem., 68(24): 4431-5.

Serrano, M., Ormazabal, A., Vilaseca, M. A., Lambruschini, N., Garcia-Romero, R., Meavilla, S., Artuch, R. (2011) Assessment of plasma ammonia and glutamine concentrations in urea cycle disorders. Clinical Biochemistry, 44(8-9): 742-744.

Stachelhaus, T. and M. A. Marahiel (1995) Modular structure of genes encoding multifunctional peptide synthetases required for non-ribosomal peptide synthesis. FEMS Microbiology Letters, 125(1): 3-14.

Szkudlinski, M., Lewinski, A, Rybicka, I., Wajs, E., & Pawlikowski, M. (1990) Glutamine derivatives as novel anticancer agents acting via gastrin binding sites. Medical Hypotheses, 32(2): 85-88.

Takahashi, H., T. Kumagai, et al. (2007) Cloning and characterization of a *Streptomyces* single module type non-ribosomal peptide synthetase catalyzing a blue pigment synthesis. J. Biol. Chem., 282(12): 9073-9081.

Tan B., Qiu Y., Zou X., Chen T., Xie G., Cheng Y., Dong T., Zhao L., Feng B., Hu X., Xu L. X., Zhao A., Zhang M., Cai G., Cai S., Zhou Z., Zheng M., Zhang Y., Jia V. (2013) Metabolomics identifies serum metabolite markers of colorectal cancer. J Proteome Res. 12: 3000-3009.

Tatiana A. et al. (1999) FEMS Microbiol Lett, 174: 247-250.

Tessaro, M. J., Soliman, S. S. M., & Raizada, M. N. (2012) Bacterial whole-cell biosensor for glutamine with applications for quantifying and visualizing glutamine in plants. Applied and Environmental Microbiology, 78(2): 604-606.

Trinh, M.-U., Blake, J., Harrison, J. R., Gerace, R., Ranieri, E., Fletcher, J. M., & Johnson, D. W. (2003) Quantification of glutamine in dried blood spots and plasma by tandem mass spectrometry for the biochemical diagnosis and monitoring of ornithine transcarbamylase deficiency. Clinical Chemistry, 49(4): 681-684.

Tsuchida, T., K. Kubota, Y. Yoshihara, K. Kikuchi, and F. Yoshinaga (1987) Fermentative production of L-glutamine by sulfaguanidine resistant mutants derived from L-glutamate producing bacteria. Agricultural and Biological Chemistry, 51(8): 2089-2094.

Tsuruoka M., Hara J., Hirayama A., Sugimoto M., Soga T., Shankle W. R., Tomita M. (2013) Capillary electrophoresis-mass spectrometry-based metabolome analysis of serum and saliva from neurodegenerative dementia patients. Electrophoresis 34: 2865-2872.

Wakisaka, Shinji, Takashi Tachiki, and Tatsurokuro Tochikura (1990) Properties of *Brevibacterium* flavum glutamine synthetase in an 'in vivo-like' system" Journal of Fermentation and Bioengineering, 70(3): 182-184.

Walsh, C. T., Gehring, A. M., Weinreb, P. H., Quadri, L. E. N., and Flugel, R. S. (1997) Curr. Opin. Chem. Biol., 1: 309-315.

Walsh, N. P., Blannin, A. K., Robson, P. J., & Gleeson, M. (1998) Glutamine, exercise and immune function. Links and possible mechanisms. Sports Medicine (NZ), 26(3): 177-191.

Walsh, C. T., et al. (2004) Science, 303: 1805-1810.

Wischmeyer, P. E. (2006) Curr Opin Clin Nutr Metab Care, 9(5): 607-12.

Yasgar et al., (2010) Mol. Biosyst., 6:365-375.

Walsh, C. T. (2007) The chemical versatility of natural-product assembly lines. Accounts of Chemical Research, 41(1): 4-10.

Young, V. R., & Ajami A. M. (2001) Glutamine: the emperor or his clothes? The Journal of Nutrition, 131(9): 2449S-2459S.

Zimmerman L., Egestad B., Jornvall H., Bergstrom J. (1989) Clin Nephrol. 32(3): 124-8.

Zou and Yin (2009) J. Am. Chem. Soc., 131:7548-7549.

Each publication, including all published books, articles, patents, and patent applications noted in this specification, is expressly and fully incorporated herein by reference.

What is claimed is:

1. A method of measuring the concentration of L-glutamine or an L-glutamine analogue in a sample obtained from a subject or a sample obtained from a bacterial or eukaryotic cell culture, the method comprising:
   incubating the sample with an activated pigment-producing NRPS (non-ribosomal peptide synthetase) under conditions to produce indigoidine pigment or an indigoidine analogue pigment; and
   quantifying the amount of the indigoidine pigment or the indigoidine analogue pigment produced in the sample by colorimetric analysis of the sample, thereby measuring the concentration of the L-glutamine or the L-glutamine analogue, respectively, in the sample, wherein at least one water-miscible solvent is added to the sample in an amount effective to dissolve the indigoidine pigment or indigoidine analogue pigment prior to quantification.

2. The method of claim 1, wherein the at least one water-miscible solvent comprises dimethylsulfoxide.

3. The method of claim 1, wherein the at least one water-miscible solvent comprises dimethylformamide.

4. The method of claim 1, wherein the pigment-producing NRPS is BpsA (blue pigment synthetase A), and wherein the BpsA is activated to the holo form prior to isolation of the BpsA.

5. The method of claim 1, wherein the pigment-producing NRPS is BpsA, and wherein the BpsA is activated to the holo form following isolation of the BpsA.

6. The method of claim 1, wherein the sample is selected from the group consisting of a blood sample, a urine sample, a saliva sample, a cerebrospinal fluid sample, a lymph fluid sample, a eukaryotic cell culture sample, a bacterial cell culture sample, and a fermentation sample.

7. The method of claim 6, wherein the sample comprises an organic co-solvent selected from the group consisting of an alcohol, a polyalcohol, dimethylformamide, and an acetonitrile.

8. The method of claim 1, wherein the glutamine analogue is selected from the group consisting of glycyl-glutamine, N-trifluoroacetyl-L-glutamine, alanyl-glutamine, indoleacetyl glutamine, N-acetylglutamine, phenylacetyl-L-glutamine, and glutamine-terminating peptides or polypeptides.

9. The method of claim 1, wherein the sample comprises a bacterial cell that synthesises L-glutamine or the glutamine analogue, and wherein an alteration in the amount of the indigoidine pigment or the indigoidine analogue pigment relative to a control or standard amount indicates altered levels of the L-glutamine or the glutamine analogue production, respectively.

10. The method of claim 9, wherein the at least one water-miscible solvent comprises dimethylsulfoxide.

11. The method of claim 9, wherein the at least one water-miscible solvent comprises dimethylformamide.

12. The method of claim 9 wherein the indigoidine pigment or indigoidine analogue pigment is dissolved in the at least one water-miscible solvent prior to quantification.

13. The method of claim 9, wherein the pigment-producing NRPS is BpsA, and wherein the BpsA is activated to the holo form prior to isolation of the BpsA.

14. The method of claim 9, wherein the pigment-producing NRPS is BpsA, and the BpsA is activated to the holo form following isolation of the BpsA.

15. The method of claim 9, wherein the bacterial cell is selected from the group consisting of a mutant cell, a variant cell, and a cell produced by targeted or random mutagenesis.

16. The method of claim 9, wherein the glutamine analogue is selected from the group consisting of a glutamine-terminating peptide, a glutamine-terminating polypeptide, and a glutamine-terminating dipeptide.

17. The method of claim 16, wherein the glutamine analogue is alanyl-glutamine.

18. The method of claim 1, wherein colorimetric analysis of the sample is carried out at 590 nm.

19. A method of measuring the concentration of L-glutamine or an L-glutamine analogue in a sample, the method comprising:
   incubating a sample obtained from a subject or a sample obtained from a bacterial or eukaryotic cell culture with an activated pigment-producing NRPS (non-ribosomal peptide synthetase) under conditions to produce indigoidine pigment or an indigoidine analogue pigment; and
   quantifying the amount of the indigoidine pigment or the indigoidine analogue pigment produced in the sample by colorimetric analysis of the sample, thereby measuring the concentration of the L-glutamine or the L-glutamine analogue, respectively, in the sample, wherein at least one water-miscible solvent is added to the sample in an amount effective to dissolve the indigoidine pigment or indigoidine analogue pigment prior to quantification.

* * * * *

SEQUENCE LISTING

```
<160> NUMBER OF SEQ ID NOS: 2

<210> SEQ ID NO 1
<211> LENGTH: 3849
<212> TYPE: DNA
<213> ORGANISM: Streptomyces lavendulae

<400> SEQUENCE: 1
atgactcttc aggagaccag cgtgctcgag cccaccctgc aggggaccac cacgttgccc      60
ggcctgctcg cccagcgggt ggccgaacac cccgaggcga tcgcggtcgc ctaccgggac     120
gacaagctca ccttccgcga gctcgcgtcc agaagcgcgg ccctcgccga ctacctggag     180
cacctcggtg tctccgccga cgactgcgtc ggcctgttcg tcgagccgtc gatcgacctg     240
atggtcggcg cctggggcat cctcaacgcc ggcgccgcgt acctgccgct gtccccggag     300
taccccgagg accggctgcg ctacatgatc gagaacagcg agacgaagat catcctggcg     360
cagcagcgcc tggtgtcccg tctgcgcgag ctcgcgccga aggacgtcac catcgtgacc     420
```

```
ctgcgcgagt ccgaggcctt cgtccgcccc gagggcaccg aggccccggc cgcccgcagc     480
gcccgcccgg acaccctcgc gtacgtcatc tacacctccg gcagcacggg caagccgaag     540
ggtgtgatga tcgagcaccg cagcatcgtc aaccagctcg gctggctgcg cgagacctac     600
gcgatcgacc gcagcaaggt catcctccag aagaccccga tgagcttcga cgccgcccag     660
tgggagatcc tctccccggc caacggcgcc accgtcgtca tgggcgcccc gggcgtctac     720
gccgaccccg agggcctcat cgagaccatc gtcaagcaca acgtgaccac cctccagtgc     780
gtcccgacgc tgctccaggg tctgatcgac accgagaagt ccccgagtgc gtctccctc      840 cagcagatct tcagcggtgg cgaggccctc tcccgcctgc tggcgatcca gaccacgcag     900
gagatgcccg ccgggcgct catcaacgtc tacgggccga ccgagacgac gatcaactcg      960
tcctcgttcc ccgtcgaccc cgccgacctg gacgagggac cgcagtccat ctccatcggc    1020
tccccggtgc acggcaccac gtaccacatc cttgacaagg agaccctcaa gccggtcggc    1080
gtcggtgaga tcggcgagct gtacatcggc ggcatccagc tggcccgcgg ctacctgcac    1140
cgcgacgacc tgaccgccga gcgcttcctg gagatcgagc tcgaggaggg cgccgagccc    1200
gtccgcctgt acaagacggg cgacctcggc cagtggaaca acgacggcac cgtgcagttc    1260 gccgccgcg ccgacaacca ggtcaagctg cgcggctacc gcgtcgagct cgacgagata     1320
tccctggcga tcgagaacca cgactgggtc cgcaacgccg ccgtcatcgt caagaacgac    1380
ggccgcaccg gcttccagaa cctgatcgcc tgcatcgagc tgagcgagaa ggaagccgcc    1440
ctgatggacc agggcaacca cggctcccac cacgcgtcga agaagagcaa gctccaggtc    1500
aaggcgcagc tgtccaaccc gggcctgcgc gacgacgccg agctggccgc ccgcccggcc    1560
ttcgacctgg agggcgccga gcccaccccc gagcagcgcg cccgggtctt cgcccgcaag    1620
acgtaccgct tctacgaggg cggcgccgtc acccaggccg acctgctggg cctgctgggc    1680
gccacggtca ccgccggcta ctcgcgcaag gcggccgacc tggccccccgc cgaactcggc    1740 cagatcctgc gctggttcgg ccagtacatc agcgaggagc ggctcctgcc gaagtacggc    1800
tacgcctccc cgggcgcgct gtacgcgacg cagatgtact tcgagctgga gggcgtcggc    1860
ggtctgaagc cgggctacta ctactaccag ccggtccgcc accagctcgt cctcatcagc    1920
gagcgcgagg ccaccggcaa ggccacggcg cagatccact tcatcggcaa gaagagcggc    1980
atcgagccgc tctacaagaa caacatcctc gaggtcctgg agatcgagac cggccacatg    2040
gtcggcctct tcgagcagat cctgccggcc tacggcctcg acatccacga ccgcgcctac    2100 gagcggccg tcaaggacct gctcgacgtc gccgacgagg actactacct gggcaccttc     2160
gagctggtcc cgcacgcggg cgcgcgcgac gaccaggccg aggtctacgt ccagacgcac    2220
ggcggaaagg tcgccggcct gcccgagggc cagtaccgct acgagaacgg cgagctgacc    2280
cgcttctcgg acgacatcgt cctcaagaag cacgtcatcg cgatcaacca gtcggtgtac    2340
caggccgcca gcttcggcat cagcgtctac agccgcgccg aggaggagtg gctgaagtac    2400
atcaccctcg gcaagaagct ccagcacctg atgatgaacg gctgaacct gggcttcatg     2460 tcctcgggct acagctccaa gacgggcaac ccgctgccgg cctcgcgccg catggacgcc    2520
gtcctcggcg ccaacggcgt cgacagcgcc ccgatgtact tcttcgtcgg cggccgcatc    2580
agcgacgagc agatcggcca cgagggcatg cgcgaggaca cgtccacat gcgcggtccg     2640 gccgagctca tccgcgacga cctcgtcagc ttcctcccgg actacatgat ccccaaccgg    2700
gtcgtggtct tcgaccggct gccgctgtcc gccaacggca agatcgacgt caaggcgctc    2760
gccgcctccg accaggtcaa cgccgagctc gtcgagcgcc ccttcgtcgc ccgcgcacg     2820
```

```
gagacggaga aggagatcgc ggcggtctgg gagaaggccc tgcgccgcga gaacgcctcc    2880
gtccaggacg acttcttcga gtcgggcggc aactcgctga tcgccgtcgg cctcgtccgc    2940
gagctcaacg cgcgcctggg cgtctccctg ccgctgcaga gcgtcctgga gtccccgacc    3000
atcgagaagc tggcccgccg cctggagcgc gaggtcgccc aggagtcctc gcgcttcgtc    3060
cgcctgcacg cggagaccgg caaggcccgg cccgtgatct gctggccggg tctgggcggc    3120
tacccgatga acctgcgcag cctggccggc gagatcggcc tcggccgctc gttctacggc    3180
gtccagtcct acggcatcaa cgagggcgag accccgtacg agaccatcac cgagatggcc    3240
aagaaggaca tcgaggccct caaggagatc cagccggccg cccctacac cctgtggggc     3300 tactccttcg gcgcccgcgt ggccttcgag accgcctacc agctggagca ggcgggcgag    3360
aaggtggaca acctcttcct gatcgccccg ggctccccga aggtgcgcgc cgagaacggc    3420
aaggtgtggg ccgcgaggc gtccttcgcc aaccgcggct acaccacgat cctgttctcg    3480
gtcttcaccg gcaccatttc cggtccggac ctggaccggt gcctggagac cgtgacggac    3540
gaggcctcct tcgccgagtt catcagcgag ctcaaggaa tcgacgtcga cctcgcccgc     3600
cggatcatct cggtcgtggg ccagacgtac gaattcgagt actccttcca cgagctggcc    3660
gagcgcaccc tccaggcgcc gatcagcatc ttcaaggccg tgggcgacga ctactcgttc    3720
ctggagaaca gcagcggcta ctcggccgag ccgccgacgg tcatcgacct cgacgccgac    3780
cactacagcc tgctgcgcga ggacatcggc gagctggtga agcacatccg ctacctgctc    3840
ggcgagtga                                                            3849

<210> SEQ ID NO 2
<211> LENGTH: 1282
<212> TYPE: PRT
<213> ORGANISM: Streptomyces lavendulae

<400> SEQUENCE: 2

Met Thr Leu Gln Glu Thr Ser Val Leu Glu Pro Thr Leu Gln Gly Thr
1               5                   10                  15

Thr Thr Leu Pro Gly Leu Leu Ala Gln Arg Val Ala Glu His Pro Glu
            20                  25                  30

Ala Ile Ala Val Ala Tyr Arg Asp Asp Lys Leu Thr Phe Arg Glu Leu
        35                  40                  45

Ala Ser Arg Ser Ala Ala Leu Ala Asp Tyr Leu Glu His Leu Gly Val
    50                  55                  60

Ser Ala Asp Asp Cys Val Gly Leu Phe Val Glu Pro Ser Ile Asp Leu
65                  70                  75                  80

Met Val Gly Ala Trp Gly Ile Leu Asn Ala Gly Ala Ala Tyr Leu Pro
                85                  90                  95

Leu Ser Pro Glu Tyr Pro Glu Asp Arg Leu Arg Tyr Met Ile Glu Asn
            100                 105                 110

Ser Glu Thr Lys Ile Ile Leu Ala Gln Gln Arg Leu Val Ser Arg Leu
        115                 120                 125

Arg Glu Leu Ala Pro Lys Asp Val Thr Ile Val Thr Leu Arg Glu Ser
    130                 135                 140

Glu Ala Phe Val Arg Pro Glu Gly Thr Glu Pro Ala Ala Arg Ser
145                 150                 155                 160

Ala Arg Pro Asp Thr Leu Ala Tyr Val Ile Tyr Thr Ser Gly Ser Thr
                165                 170                 175

Gly Lys Pro Lys Gly Val Met Ile Glu His Arg Ser Ile Val Asn Gln
```

```
                180                 185                 190
Leu Gly Trp Leu Arg Glu Thr Tyr Ala Ile Asp Arg Ser Lys Val Ile
            195                 200                 205

Leu Gln Lys Thr Pro Met Ser Phe Asp Ala Ala Gln Trp Glu Ile Leu
        210                 215                 220

Ser Pro Ala Asn Gly Ala Thr Val Val Met Gly Ala Pro Gly Val Tyr
225                 230                 235                 240

Ala Asp Pro Glu Gly Leu Ile Glu Thr Ile Val Lys His Asn Val Thr
                245                 250                 255

Thr Leu Gln Cys Val Pro Thr Leu Leu Gln Gly Leu Ile Asp Thr Glu
            260                 265                 270

Lys Phe Pro Glu Cys Val Ser Leu Gln Gln Ile Phe Ser Gly Gly Glu
        275                 280                 285

Ala Leu Ser Arg Leu Leu Ala Ile Gln Thr Thr Gln Glu Met Pro Gly
    290                 295                 300

Arg Ala Leu Ile Asn Val Tyr Gly Pro Thr Glu Thr Thr Ile Asn Ser
305                 310                 315                 320

Ser Ser Phe Pro Val Asp Pro Ala Asp Leu Asp Glu Gly Pro Gln Ser
                325                 330                 335

Ile Ser Ile Gly Ser Pro Val His Gly Thr Thr Tyr His Ile Leu Asp
            340                 345                 350

Lys Glu Thr Leu Lys Pro Val Gly Val Gly Glu Ile Gly Glu Leu Tyr
        355                 360                 365

Ile Gly Gly Ile Gln Leu Ala Arg Gly Tyr Leu His Arg Asp Asp Leu
    370                 375                 380

Thr Ala Glu Arg Phe Leu Glu Ile Glu Leu Glu Gly Ala Glu Pro
385                 390                 395                 400

Val Arg Leu Tyr Lys Thr Gly Asp Leu Gly Gln Trp Asn Asn Asp Gly
                405                 410                 415

Thr Val Gln Phe Ala Gly Arg Ala Asp Asn Gln Val Lys Leu Arg Gly
            420                 425                 430

Tyr Arg Val Glu Leu Asp Glu Ile Ser Leu Ala Ile Glu Asn His Asp
        435                 440                 445

Trp Val Arg Asn Ala Ala Val Ile Val Lys Asn Asp Gly Arg Thr Gly
    450                 455                 460

Phe Gln Asn Leu Ile Ala Cys Ile Glu Leu Ser Glu Lys Glu Ala Ala
465                 470                 475                 480

Leu Met Asp Gln Gly Asn His Gly Ser His His Ala Ser Lys Lys Ser
                485                 490                 495

Lys Leu Gln Val Lys Ala Gln Leu Ser Asn Pro Gly Leu Arg Asp Asp
            500                 505                 510

Ala Glu Leu Ala Ala Arg Pro Ala Phe Asp Leu Glu Gly Ala Glu Pro
        515                 520                 525

Thr Pro Glu Gln Arg Ala Arg Val Phe Ala Arg Lys Thr Tyr Arg Phe
    530                 535                 540

Tyr Glu Gly Gly Ala Val Thr Gln Ala Asp Leu Leu Gly Leu Leu Gly
545                 550                 555                 560

Ala Thr Val Thr Ala Gly Tyr Ser Arg Lys Ala Ala Asp Leu Ala Pro
                565                 570                 575

Ala Glu Leu Gly Gln Ile Leu Arg Trp Phe Gly Gln Tyr Ile Ser Glu
            580                 585                 590

Glu Arg Leu Leu Pro Lys Tyr Gly Tyr Ala Ser Pro Gly Ala Leu Tyr
        595                 600                 605
```

-continued

```
Ala Thr Gln Met Tyr Phe Glu Leu Glu Gly Val Gly Gly Leu Lys Pro
    610             615                 620
Gly Tyr Tyr Tyr Gln Pro Val Arg His Gln Leu Val Leu Ile Ser
625             630                 635                 640
Glu Arg Glu Ala Thr Gly Lys Ala Thr Ala Gln Ile His Phe Ile Gly
                645                 650                 655
Lys Lys Ser Gly Ile Glu Pro Val Tyr Lys Asn Asn Ile Leu Glu Val
                660                 665                 670
Leu Glu Ile Glu Thr Gly His Met Val Gly Leu Phe Glu Gln Ile Leu
            675                 680                 685
Pro Ala Tyr Gly Leu Asp Ile His Asp Arg Ala Tyr Glu Pro Ala Val
690                 695                 700
Lys Asp Leu Leu Asp Val Ala Asp Glu Asp Tyr Tyr Leu Gly Thr Phe
705                 710                 715                 720
Glu Leu Val Pro His Ala Gly Ala Arg Asp Asp Gln Ala Glu Val Tyr
                725                 730                 735
Val Gln Thr His Gly Gly Lys Val Ala Gly Leu Pro Glu Gly Gln Tyr
            740                 745                 750
Arg Tyr Glu Asn Gly Glu Leu Thr Arg Phe Ser Asp Asp Ile Val Leu
        755                 760                 765
Lys Lys His Val Ile Ala Ile Asn Gln Ser Val Tyr Gln Ala Ala Ser
770                 775                 780
Phe Gly Ile Ser Val Tyr Ser Arg Ala Glu Glu Trp Leu Lys Tyr
785                 790                 795                 800
Ile Thr Leu Gly Lys Lys Leu Gln His Leu Met Met Asn Gly Leu Asn
                805                 810                 815
Leu Gly Phe Met Ser Ser Gly Tyr Ser Ser Lys Thr Gly Asn Pro Leu
            820                 825                 830
Pro Ala Ser Arg Arg Met Asp Ala Val Leu Gly Ala Asn Gly Val Asp
            835                 840                 845
Ser Ala Pro Met Tyr Phe Phe Val Gly Gly Arg Ile Ser Asp Glu Gln
        850                 855                 860
Ile Gly His Glu Gly Met Arg Glu Asp Ser Val His Met Arg Gly Pro
865                 870                 875                 880
Ala Glu Leu Ile Arg Asp Asp Leu Val Ser Phe Leu Pro Asp Tyr Met
                885                 890                 895
Ile Pro Asn Arg Val Val Val Phe Asp Arg Leu Pro Leu Ser Ala Asn
            900                 905                 910
Gly Lys Ile Asp Val Lys Ala Leu Ala Ala Ser Asp Gln Val Asn Ala
        915                 920                 925
Glu Leu Val Glu Arg Pro Phe Val Ala Pro Arg Thr Glu Thr Glu Lys
    930                 935                 940
Glu Ile Ala Ala Val Trp Glu Lys Ala Leu Arg Arg Glu Asn Ala Ser
945                 950                 955                 960
Val Gln Asp Asp Phe Phe Glu Ser Gly Gly Asn Ser Leu Ile Ala Val
                965                 970                 975
Gly Leu Val Arg Glu Leu Asn Ala Arg Leu Gly Val Ser Leu Pro Leu
            980                 985                 990
Gln Ser Val Leu Glu Ser Pro Thr Ile Glu Lys Leu Ala Arg Arg Leu
        995                 1000                1005
Glu Arg Glu Val Ala Gln Glu Ser Ser Arg Phe Val Arg Leu His
    1010                1015                1020
```

```
Ala Glu Thr Gly Lys Ala Arg Pro Val Ile Cys Trp Pro Gly Leu
    1025                1030                1035
Gly Gly Tyr Pro Met Asn Leu Arg Ser Leu Ala Gly Glu Ile Gly
    1040                1045                1050
Leu Gly Arg Ser Phe Tyr Gly Val Gln Ser Tyr Gly Ile Asn Glu
    1055                1060                1065
Gly Glu Thr Pro Tyr Glu Thr Ile Thr Glu Met Ala Lys Lys Asp
    1070                1075                1080
Ile Glu Ala Leu Lys Glu Ile Gln Pro Ala Gly Pro Tyr Thr Leu
    1085                1090                1095
Trp Gly Tyr Ser Phe Gly Ala Arg Val Ala Phe Glu Thr Ala Tyr
    1100                1105                1110
Gln Leu Glu Gln Ala Gly Glu Lys Val Asp Asn Leu Phe Leu Ile
    1115                1120                1125
Ala Pro Gly Ser Pro Lys Val Arg Ala Glu Asn Gly Lys Val Trp
    1130                1135                1140
Gly Arg Glu Ala Ser Phe Ala Asn Arg Gly Tyr Thr Thr Ile Leu
    1145                1150                1155
Phe Ser Val Phe Thr Gly Thr Ile Ser Gly Pro Asp Leu Asp Arg
    1160                1165                1170
Cys Leu Glu Thr Val Thr Asp Glu Ala Ser Phe Ala Glu Phe Ile
    1175                1180                1185
Ser Glu Leu Lys Gly Ile Asp Val Asp Leu Ala Arg Arg Ile Ile
    1190                1195                1200
Ser Val Val Gly Gln Thr Tyr Glu Phe Glu Tyr Ser Phe His Glu
    1205                1210                1215
Leu Ala Glu Arg Thr Leu Gln Ala Pro Ile Ser Ile Phe Lys Ala
    1220                1225                1230
Val Gly Asp Asp Tyr Ser Phe Leu Glu Asn Ser Ser Gly Tyr Ser
    1235                1240                1245
Ala Glu Pro Pro Thr Val Ile Asp Leu Asp Ala Asp His Tyr Ser
    1250                1255                1260
Leu Leu Arg Glu Asp Ile Gly Glu Leu Val Lys His Ile Arg Tyr
    1265                1270                1275
Leu Leu Gly Glu
    1280
```